(12) United States Patent
Kim et al.

(10) Patent No.: US 11,617,806 B2
(45) Date of Patent: Apr. 4, 2023

(54) MASK STORAGE APPARATUS

(71) Applicant: LG ELECTRONICS INC., Seoul (KR)

(72) Inventors: Youngjun Kim, Seoul (KR); Nameun Cho, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 838 days.

(21) Appl. No.: 16/657,624

(22) Filed: Oct. 18, 2019

(65) Prior Publication Data

US 2020/0129650 A1 Apr. 30, 2020

(30) Foreign Application Priority Data

| Oct. 30, 2018 | (KR) | ......................... 10-2018-0130671 |
| Dec. 10, 2018 | (KR) | ......................... 10-2018-0158477 |
| Dec. 13, 2018 | (KR) | ......................... 10-2018-0161030 |
| Jul. 23, 2019 | (KR) | ......................... 10-2019-0089168 |

(51) Int. Cl.
*A61L 2/10* (2006.01)
*A41D 13/11* (2006.01)
*A62B 23/02* (2006.01)

(52) U.S. Cl.
CPC ................ *A61L 2/10* (2013.01); *A41D 13/11* (2013.01); *A62B 23/025* (2013.01); *A61L 2202/122* (2013.01)

(58) Field of Classification Search
CPC ..... A61L 2/10; A61L 2202/122; A41D 13/11; A62B 23/025
See application file for complete search history.

(56) References Cited

U.S. PATENT DOCUMENTS

| 5,881,877 | A | 3/1999 | Adams |
| 6,780,383 | B1 | 8/2004 | Ettlinger et al. |
| 2012/0227745 | A1 | 9/2012 | Arcilla et al. |
| 2013/0233874 | A1* | 9/2013 | Sundnes ............ B65D 21/0233 220/834 |

FOREIGN PATENT DOCUMENTS

| CN | 1802188 A | 7/2006 |
| CN | 103025444 A | 4/2013 |
| CN | 104018326 A | 9/2014 |
| CN | 203954237 U | 11/2014 |
| CN | 204635354 U | 9/2015 |
| CN | 206646297 U | 11/2017 |

(Continued)

OTHER PUBLICATIONS

Machine Translation for CN207323742; Inventor: Lin (Year: 2018).*

*Primary Examiner* — Sean E Conley
(74) *Attorney, Agent, or Firm* — Dentons US LLP

(57) ABSTRACT

A mask storage apparatus includes a body including an accommodation space in which a mask device is stored. A cover is rotatably connected to the body and is capable of opening and closing the accommodation space. A compartment extends from an inner surface of the body and partitions the accommodation space into a first accommodation space in which a part of the mask device is accommodated, and a second accommodation space in which a remaining part of the mask device is accommodated. The compartment includes a sterilization module to sterilize the mask device.

20 Claims, 18 Drawing Sheets

(56) References Cited

FOREIGN PATENT DOCUMENTS

| | | |
|---|---|---|
| CN | 107462036 A | 12/2017 |
| CN | 206822971 U | 1/2018 |
| CN | 207323742 U | 5/2018 |
| EP | 3264934 A1 | 1/2018 |
| EP | 3326675 A1 | 5/2018 |
| JP | 2005000613 A | 1/2005 |
| JP | 2011137433 A | 7/2011 |
| JP | 2012081215 A | 4/2012 |
| JP | 2013048715 A | 3/2013 |
| KR | 20-0348505 A | 4/2004 |
| KR | 20-0354992 A | 7/2004 |
| KR | 1020100060832 A | 6/2010 |
| KR | 101148973 B1 | 5/2012 |
| KR | 101832472 B1 | 2/2018 |
| TW | 201206788 A1 | 2/2012 |
| WO | 2016142232 A1 | 9/2016 |

\* cited by examiner

MASK STORAGE APPARATUS

CROSS-REFERENCE TO RELATED APPLICATIONS

This application claims the benefit of priority to Korean Patent Application Nos. 10-2018-0130671 filed on Oct. 30, 2018; 10-2018-0158477 filed on Dec. 10, 2018; 10-2018-0161030 filed on Dec. 13, 2018; and 10-2019-0089168 filed on Jul. 23, 2019; the entire contents of which are incorporated herein by reference.

FIELD OF THE DISCLOSURE

The present disclosure relates to mask storage apparatus.

BACKGROUND

In general, a mask refers to a device covering a user's nose and mouth to prevent inhalation of germs, dust, and the like. The mask is usually in close contact with the user's face to cover the user's nose and mouth. The mask filters germs, dust, and the like contained in the air flowing into the user's nose and mouth, and allows the user to breath in filtered air. Germs, dust, and the like contained in the air pass through a body of the mask that includes a filter, and the germs, dust and the like are filtered by the body of the mask.

However, the germs, dust, and the like filtered by the mask may attach to the body of the mask and contaminate the mask body. Therefore, in order to reuse the mask, the attached foreign matter should be removed manually or cleaned using a cleaning device.

An example of a mask storage case may be found in Korean Utility Model Registration No. 20-0354992. A technique for storing a mask inside the mask storage case includes sterilizing the mask from bacteria adhered to the mask. The mask storage case is manufactured by mixing any one of tourmaline powder, nanosilver, photocatalyst, and copper in order to sterilize the mask.

Another example of a mask storage case may be found in Korean Utility Model Registration No. 20-0348505. A technique for storing a mask inside the mask storage case includes sterilizing the mask from bacteria adhered to the mask. The mask storage case may sterilize the mask from bacteria adhered to the mask by including a functional panel having a sterilization function at an inner surface where the mask may be stored.

SUMMARY

One aspect is to provide a mask storage apparatus capable of stably storing a mask device and effectively removing bacteria, contaminants, etc., present in the mask device.

Another aspect is to provide a mask storage apparatus where the mask device may be kept relatively fixed in the mask storage apparatus so that damage to the mask device due to the movement of the mask storage device may be minimized.

Another aspect is to provide a mask storage apparatus that may quickly dry and ventilate a mask device while the mask device is stored in the mask storage apparatus Another aspect is to provide a mask storage apparatus that is easy to install and detach an air module for forced blowing.

Another aspect is to provide a mask storage apparatus in which sterilizing light generated by a sterile lamp may be effectively irradiated to a specific portion of the mask device.

Another aspect is to provide a mask storage apparatus capable of charging the battery of the mask device while the mask device is stored.

The disclosure discloses a mask storage apparatus that includes a body including; an accommodation space in which a mask device is stored, a cover rotatably connected to the body and capable of opening and closing the accommodation space, and a compartment extending from an inner surface of the body and partitioning the accommodation space into a first accommodation space in which a part of the mask device is accommodated, and a second accommodation space in which a remaining part of the mask device is accommodated, where the compartment including a sterilization module to sterilize the mask device,

DETAILED DESCRIPTION OF THE PREFERRED EMBODIMENTS

Figure 1:
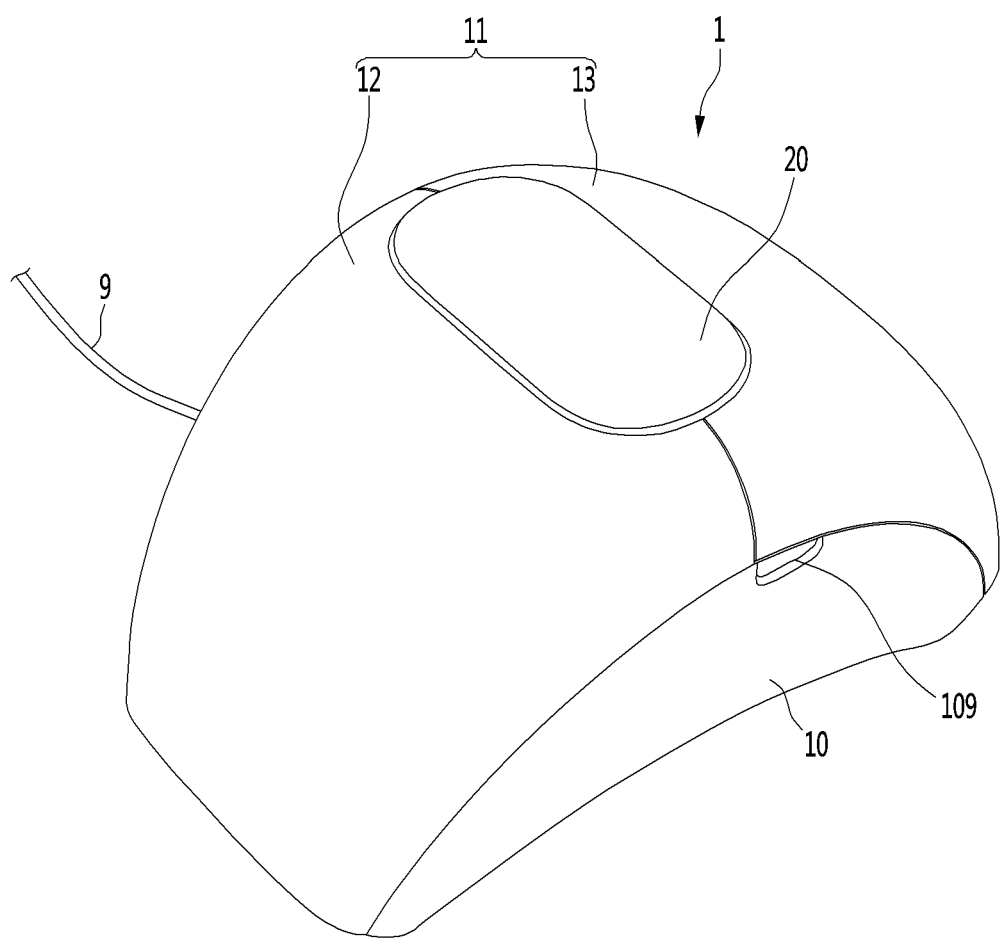
FIG. 1 is a perspective view of a mask storage apparatus according to a first embodiment of the present invention.

Hereinafter, preferred embodiments of the present invention will be described in detail through exemplary drawings. In adding reference numerals to the components of the drawings, it should be noted that the same reference numerals may be used even though they are shown in different drawings. In addition, in describing the embodiments of the present invention, if it is determined that the detailed description of the well-known configuration or function interferes with the understanding of the embodiments of the present invention, the detailed description thereof may be omitted.

In addition, in describing the components of the embodiment of the present invention, terms such as first, second, A, B, (a), and (b) may be used. These terms are for distinguishing the components from other components, and the nature, order or order of the components are not limited to the terms. If a component is described as being "connected", "coupled" or "connected" to another component, it should be understood that the component may be directly connected or connected to that other component, but having other components there between.

Figure 2:
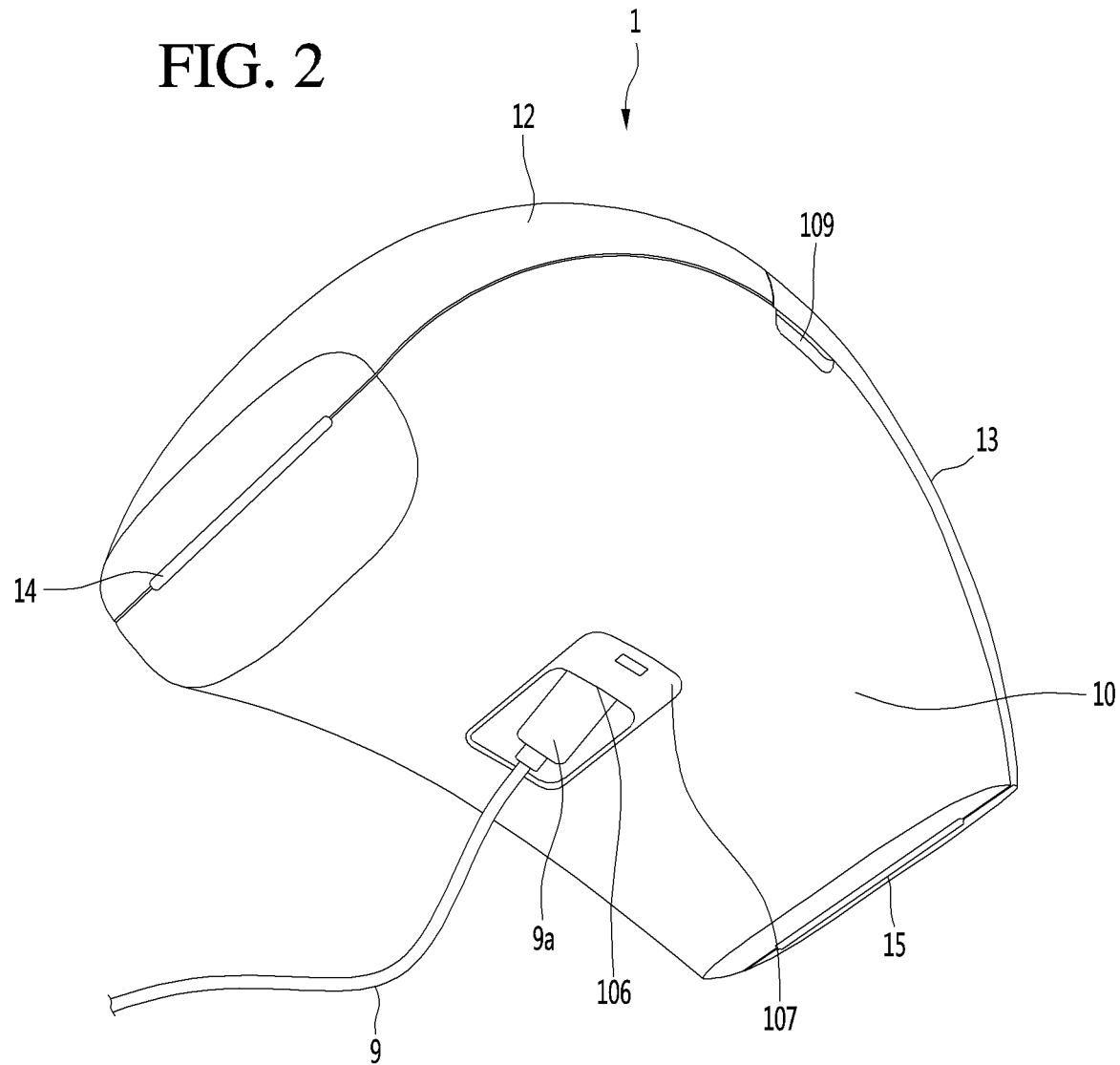
FIG. 2 is a bottom view of the mask storage apparatus according to the first embodiment of the present invention.
Figure 3:
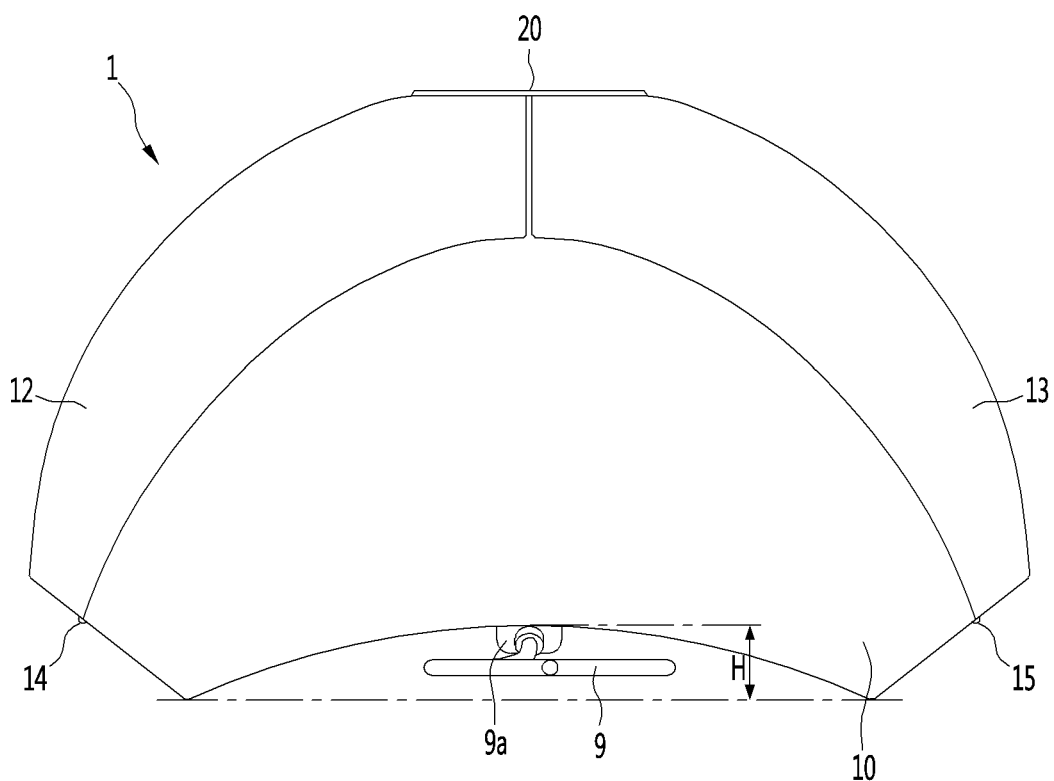
FIG. 3 is a front view of the mask storage apparatus according to the first embodiment of the present invention.
Figure 4:
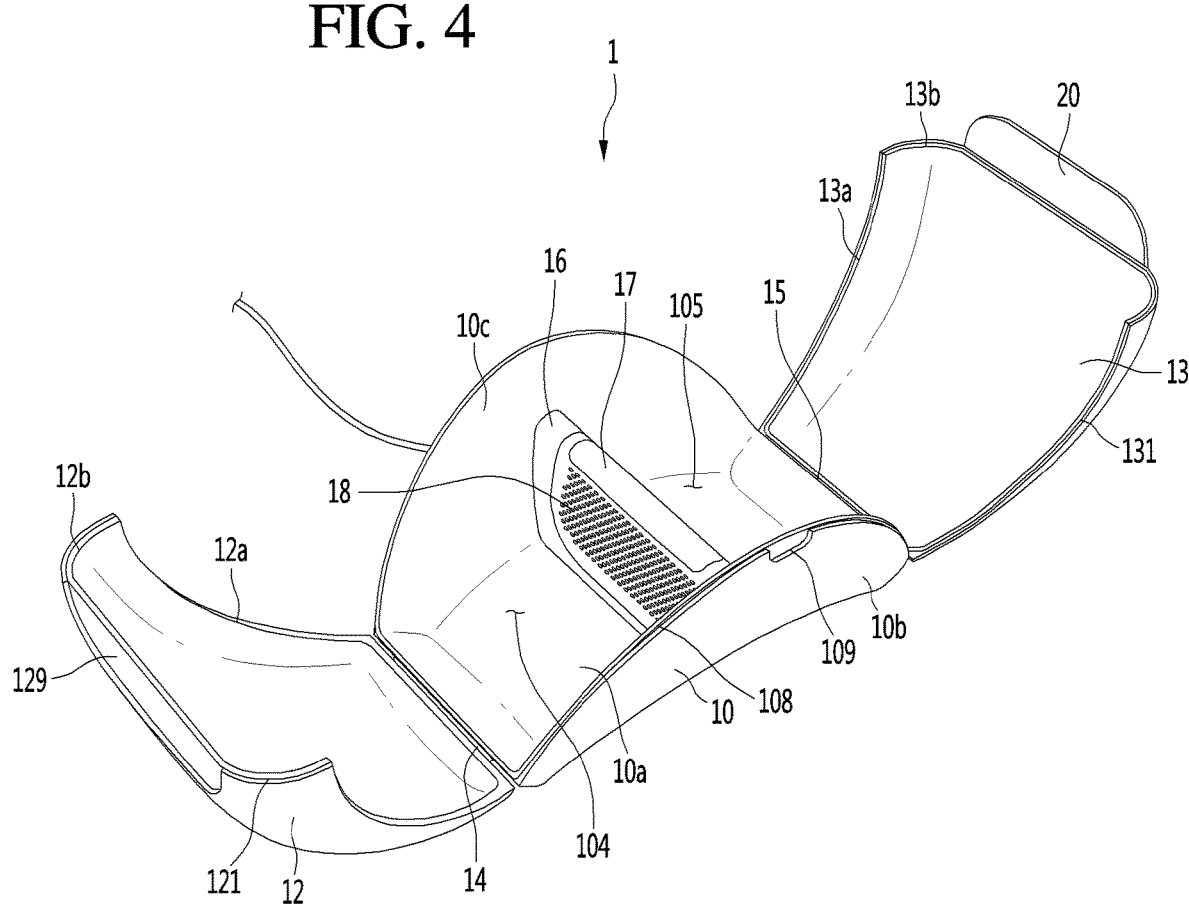
FIG. 4 is a view showing an open state of the mask storage apparatus according to the first embodiment of the present invention.
Figure 5:
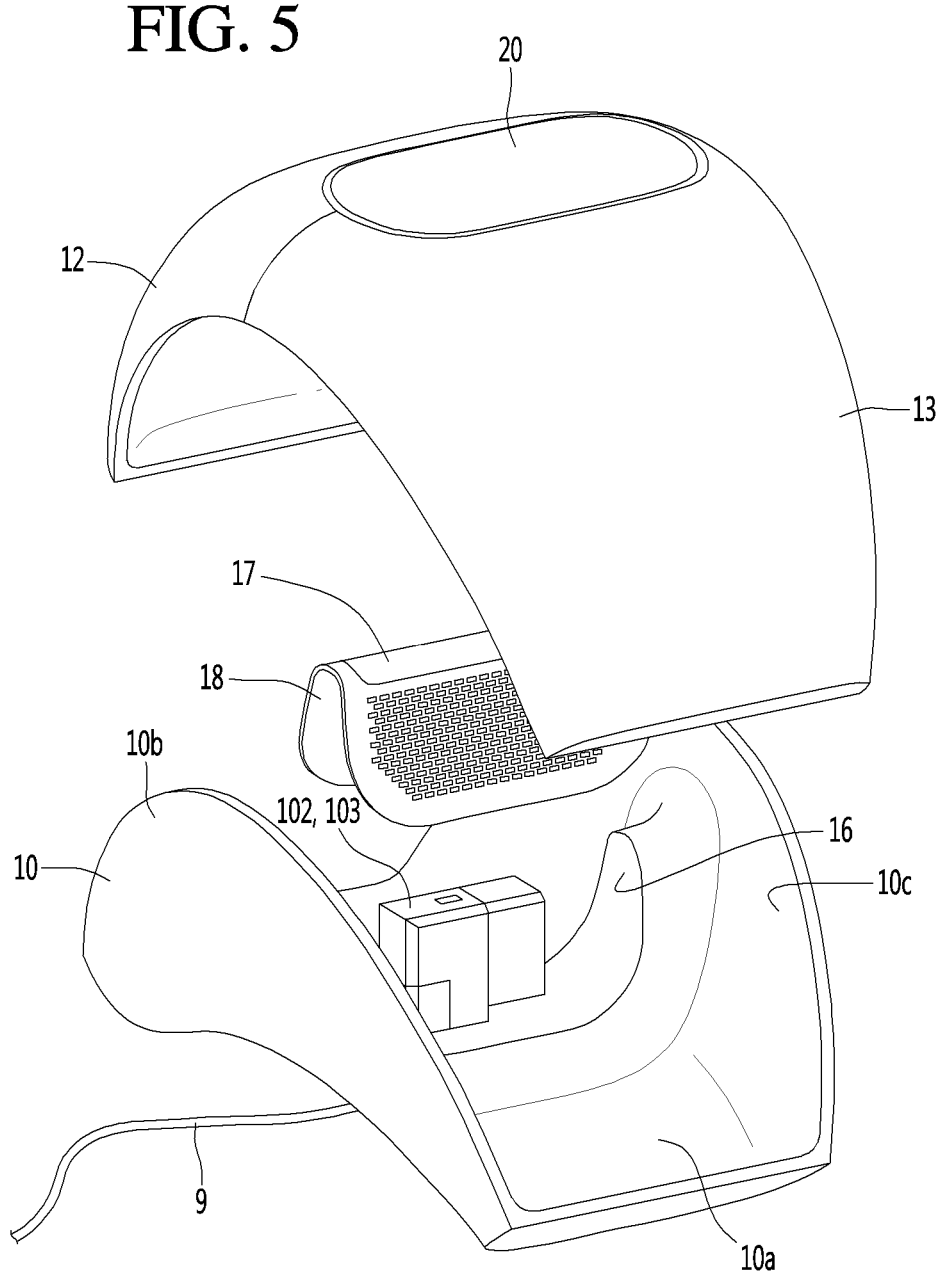
FIG. 5 is an exploded perspective view of the mask storage apparatus according to the first embodiment of the present invention.
Figure 6:
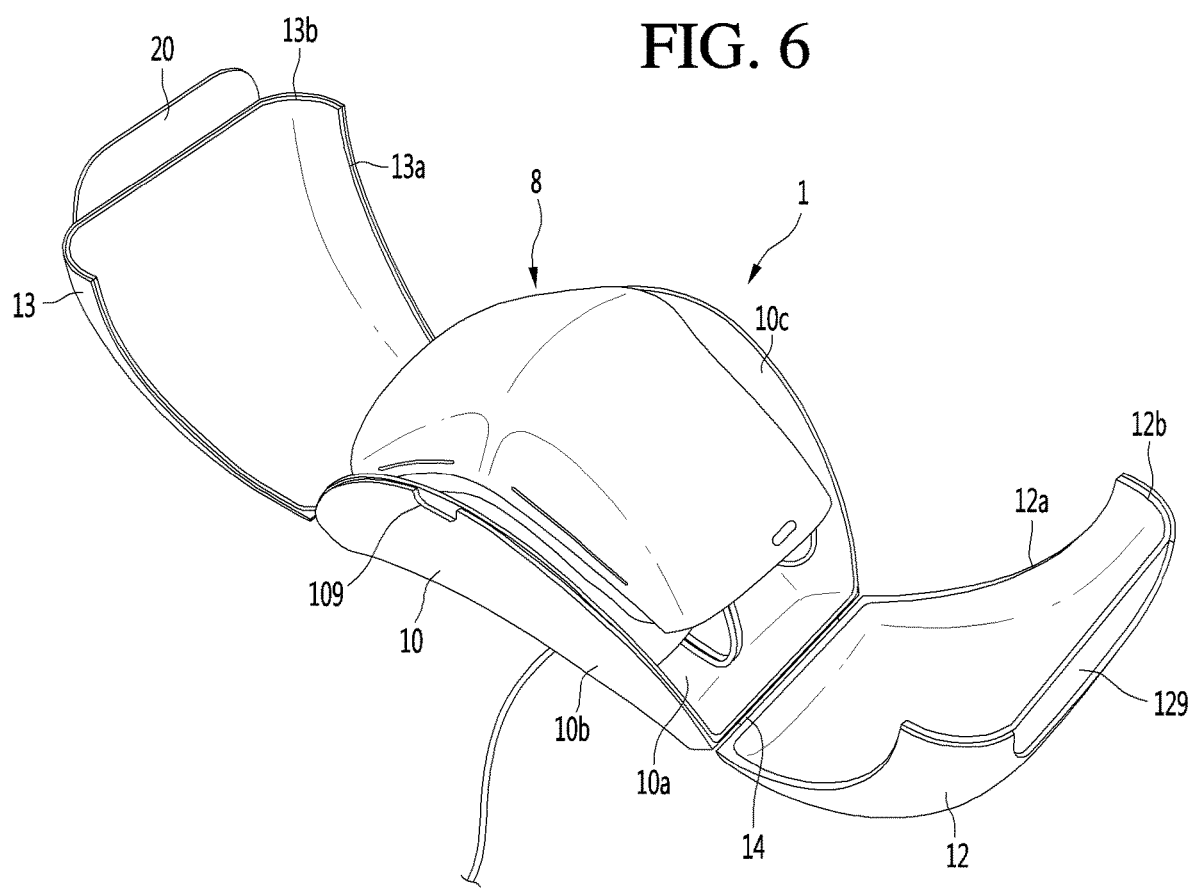
FIG. 6 is a view showing a state in which a mask device is stored in the mask storage apparatus according to the first embodiment of the present invention.

FIG. 1 is a perspective view of a mask storage apparatus according to a first embodiment of the present invention, FIG. 2 is a bottom view of a mask storage apparatus according to the first embodiment of the present invention, FIG. 3 is a front view of the mask storage apparatus according to the first embodiment of the present invention, FIG. 4 is a view showing an open state of the mask storage apparatus according to the first embodiment of the present invention, FIG. 5 is an exploded perspective view of the mask storage apparatus according to the first embodiment of the present invention, and FIG. 6 is a view showing a state in which a mask device is stored in a mask storage apparatus according to the first embodiment of the present invention.

Referring to FIGS. 1 to 6, a mask storage apparatus 1 is configured to store a mask device 8 therein. Here, the mask device 8 may be a device that covers the user's nose and mouth, and prevents foreign substances from entering the user's nose and mouth.

The mask storage apparatus 1 may include a device storage body 10 and a device storage cover 11 that covers a portion of the device storage body 10, in this case an upper surface of the device storage body 10. The device storage cover 11 may open or close the device storage body 10. An accommodation space in which the mask device 8 may be accommodated may be formed in the device storage body 10.

When the device storage cover 11 is opened, the mask device 8 may be introduced into the accommodation space of the device storage body 10. When the mask device 8 is inserted into the accommodation space, the device storage cover 11 may be closed in order to protect the mask device 8 from the outside environment including germs, dust and the like.

The device storage body 10 includes a bottom surface 10*a* that may be supported on the ground and side surfaces 10*b* and 10*c* extending upward from the bottom surface 10*a*. The device storage body 10 may have an open top and side surfaces.

The bottom surface 110*a* may be formed with sufficient area so that the mask device 8 may be supported. The bottom surface 10*a* may be partially spaced upward from the ground. For example, the bottom surface 10*a* may be formed in a convex shape.

For example, the bottom surface 10*a* may have a shape which is convex with respect to both end portions thereof going towards the center. In the present embodiment, the bottom surface 10*a* may include a round surface having a constant radius of curvature.

The side surfaces 10*b* and 10*c* extend upward from the edge of the bottom surface 10*a*. The side surfaces 10*b* and 10*c* prevent the mask device 8 supported on the bottom surface 10*a* from deviating at the sides of the device storage body 10. The side surfaces 10*b* and 10*c* protrude from a portion of the edge of the bottom surface 10*a* to a predetermined height to support the mask device 8 from the sides.

In the present embodiment, the side surfaces 10*b* and 10*c* include a first side surface 10*b* and a second side surface 10*c* extending upward in the longitudinal direction at the edge of the bottom surface 10*a*.

The first side surface 10*b* extends upward along the longitudinal direction from a first edge of the bottom surface 10*a*, and the second side surface 10*c* extends upwards along the longitudinal direction at a second edge of the bottom surface 10*a*. Accordingly, the first side surface 10*b* and the second side surface 10*c* are disposed to face each other.

Each end of the first side surface 10*b* and the second side surface 10*c* may be rounded. For example, an upper end of each of the first side surface 10*b* and the second side surface 10*c* may be rounded to have a predetermined curvature. The first side surface 10*b* and the second side surface 10*c* may have a semicircle or half-moon shape. The rounded upper end portion of the first side surface 10*b* and the second side surface 10*c* may be in contact with the device storage cover 11 to be described later.

In the present embodiment, the device storage body 10 may be formed in a basket or container shape in which the mask device 8 may be stored. For example, a portion of the device storage body 10 may be formed to be recessed in which a portion of the mask device 8 may seat.

The device storage body 10 may be formed to correspond to the shape of the mask device 8. The device storage body 10 may be formed in a semicircle, fan-shape, bow-shape, and the like. For example, the device storage body 10 may be formed so that the mask device 8 may be stored in the accommodation space of the device storage body 10 without overlapping.

The device storage cover 11 may include one or more covers. In the present embodiment, the device storage cover 11 may include a first cover 12 and a second cover 13. The first cover 12 may be disposed on one side of the device storage body 10 and may be rotatable with respect to the device body 10. The second cover 13 may be disposed on the other side of the storage device body 10 and may be similarly rotatably provided.

The first cover 12 may cover a portion of the accommodation space of the device storage cover 11. The second cover 13 may cover the remaining part of the accommodation space of the storage device cover 11. That is, when the first cover 12 and the second cover 13 are closed, the accommodation space of the storage device body 10 may be closed to the outside environment.

The first cover 12 may cover a predetermined area and may be rounded. The first cover 12 may be connected to one side of the device storage body 10 and may be provided to cover an upper portion of the storage device body 10. In this case, the first cover 12 is formed in a shape corresponding to a portion in contact with the device storage body 10, that is, a portion of the side surfaces 10*b* and 10*c* of the device storage body 10.

The first cover 12 includes a first edge 12*a* formed with a curvature corresponding to the upper end portions of the side surfaces 10*b* and 10*c*. The first edge 12*a* extends along the edge of the first cover 12 and has the same or similar radius of curvature as the upper end portions of the side surfaces 10*b* and 10*c*. Therefore, when the first cover 12 is closed, the first edge 12*a* may make close contact with the upper end portions of the side surfaces 10*b* and 10*c*. In this case, the first edge 12*a* may follow the contour of the upper end portions of the side surfaces 10*b* and 10*c* for tight contact without gaps there between.

The second cover 13 may cover a predetermined area and may be rounded. The second cover 13 may be connected to the other side of the device storage body 10 and may be provided to cover an upper portion of the device storage device body 10. In this case, the second cover 13 is formed in a shape corresponding to a portion in contact with the device storage device body 10, that is, the other upper end portions of the side surfaces 10*b* and 10*c* of the device storage body 10.

The second cover 13 includes a first edge 13*a* formed with a curvature corresponding to the other upper end portions of the side surfaces 10*b* and 10*c*. The first edge 13*a* extends along the edge of the second cover 13 and has the same radius of curvature as the other upper end portions of the side surfaces 10*b* and 10*c*. Therefore, when the second cover 12 is closed, the first edge 13*a* may make close contact with the other upper end portions of the side surfaces 10*b* and 10*c*. In this case, the first edge 13*a* may follow the contour of the other upper end portions of the side surfaces 10*b* and 10*c* for tight contact without gaps there between.

The first cover 12 and the second cover 13 may be formed to be symmetrical to each other.

The first cover 12 and the second cover 13 further include second edges 12*b* and 13*b*, respectively. The second edges 12*b* and 13*b* form portions of the first cover 12 and the second cover 13 that make contact with each other. That is, when both the first cover 12 and the second cover 13 are closed, the second edge 12*b* of the first cover 12 and the second edge 13*b* of the second cover 13 make face to face contact with each other to close without gaps there between.

With this cover configuration, the inner space of the storage device body 10 may be completely closed to the outside environment by the device storage cover 11. In addition, the outer surface of the mask storage apparatus 1 may be made aesthetically pleasing by the smooth rounded edge of the device storage cover 11.

In the present embodiment, the device storage cover 11 is described as including first and second covers, however the device storage cover 11 may include one or three or more covers. For example, the device storage cover 11 may include one cover, and the one cover may cover the entire accommodation space of the device storage body 10.

Alternatively, the device storage cover 11 may include first, second and third covers, and the accommodation space of the device storage body 10 may be covered by the first, second and third covers.

The device storage body 10 may include one or more hinges. In the present embodiment, the storage device body 10 may include a first hinge 14 and a second hinge 15.

The first hinge 14 may connect one side of the device storage body 10 and one end of the first cover 12. The second hinge 15 may connect the other side of the device storage body 10 and one end of the second cover 13. The first hinge 14 may allow the first cover 12 to rotate relative to one side of the device storage device body 10. The second hinge 15 may allow the second cover 13 to rotate relative to the other side of the device storage body 10.

The first hinge 14 and the second hinge 15 may be located at both sides of the bottom surface 10*a* of the device storage device body 10, respectively. In this case, the rotational direction of the first hinge 14 and the rotational direction of the second hinge 15 may be opposite to each other. That is, the first cover 12 and the second cover 130 may rotate in a direction approaching each other to close the accommodation space, and rotate in a direction away from each other to open the accommodation space. Accordingly, the device storage cover 11 may be quickly opened and the space occupied by the device storage cover 11 may be minimized when opened.

The device storage body 10 and the device storage cover 11 may include one or more coupling ribs. The coupling ribs may function to fix the device storage cover 11 so as not to open from the device storage body 10 without external force. Alternatively, the coupling ribs may function to seal the accommodation space of the device storage body 10.

In the present embodiment, the coupling ribs include a first coupling rib 108 provided on the device storage body 10, a second coupling rib 121 provided on the first cover 12, and a third coupling rib 131 provided on the second cover 13.

When the device storage cover 11 rotates to close on the device storage body 10, the coupling ribs provided on the device storage cover 11 and the device storage body 10 may be coupled to each other. That is, when the device storage cover 11 closes on the device storage body 10, the first coupling rib 108 may couple with the second coupling rib 121 and the third coupling rib 131 and may seal the accommodation space of the storage device body 10.

The first coupling rib 108 may be provided on an inner surface or an edge of the device storage body 10. In one example, the first coupling rib 108 may be provided at the upper end of the sides 10*b*, 10*c* of the device storage device body 10.

The second coupling rib 121 may be provided on an inner surface or an edge of the first cover 12. The second coupling rib 121 may be provided on an inner surface or an edge of the first cover 12 corresponding to the position of the first coupling rib 108. For example, the second coupling rib 121 may be formed on at least one of the first edge 12*a* and the second edge 12*b* of the first cover 12.

The third coupling rib 131 may be provided on an inner surface or an edge of the second cover 13. The third coupling rib 131 may be provided on an inner surface or an edge of the second cover 13 corresponding to the position of the first coupling rib 108. For example, the third coupling rib 131 may be formed on at least one of the first edge 13*a* and the second edge 13*b* of the second cover 13.

Accordingly, when the device storage cover 11 closes on the device storage body 10, the second coupling rib 121 and the third coupling rib 131 are fittingly coupled to the first coupling rib 108 and may be fixed. The first coupling rib 108 may be formed in a shape corresponding to the second coupling rib 121 and the third coupling rib 131.

The first coupling rib 108 may be formed by recessing a portion of the edge of the device storage body 10. The second coupling rib 121 may be formed by recessing a portion of the edge of the first cover 12. The third coupling rib 131 may be formed by recessing a portion of the edge of the second cover 13.

The second coupling rib 121 may be coupled to a portion of the first coupling rib 108, and the third coupling rib 131 may be coupled to the remaining portion of the first coupling rib 108. In the present embodiment, the coupling ribs being fitted and fixed are described and the accommodation space of the device storage device body 10 is described as being sealed, but a gasket inserted between the device storage body 10 and the device storage cover 11 is also possible to enhance sealing, for example.

The device storage cover 11 may include a display 20. The display 20 may indicate an operating state of the mask storage device 1. The display 20 may be provided in any one of the first cover 12 and the second cover 13. In the present embodiment, the display 20 seats on both the first cover 12 and the second cover 13. In this case, the display 20 may be provided on one of the first cover 12 and the second cover 13, and the other one of the first cover 12 and the second cover 13 may be provided with a display seating recess 129 on which the display 20 may be seated.

In the present embodiment, the display 20 is provided on the second cover 13, and the display seating recess 129 is provided on the first cover 12. The display 20 may be mounted on an outer surface of the second cover 13 so that the user may see the display 20 while the second cover 13 is closed.

Here, the outer surface of the second cover 13 refers to the surface of the second cover 13 that is exposed to the outside environment in a state in which the second cover 13 is closed. Conversely, the inner surface of the second cover 13 refers the surface of the second cover 13 facing the inside of the mask storage apparatus 1 in a state where the second cover 13 is closed. That is, the inner surface of the second cover 13 is not exposed to the outside environment while the second cover 13 is closed.

The display 20 may be installed so that at least a portion thereof covers the outer surface of the second cover 13. In other words, a part of the display 20 may be fixed to the second cover 13, and the other part may be free with respect to the second cover 13. The display 20 may be disposed at an end portion of the second cover 13.

The display seating recess 129 may be provided in the first cover 12. The display seating recess 129 may be recessed inward from an outer surface of the first cover 12. For example, the display seating recess 129 may be formed by recessing a portion of the outer surface of the first cover 12 toward the inner surface of the first cover 12.

Here, the outer surface of the first cover 12 refers a surface of the first cover 12 that is exposed to the outside environment in a state where the first cover 12 is closed. Conversely, the inner surface of the first cover 12 refers to the surface of the first cover 12 facing the inside of the mask storage apparatus 1 in a state where the first cover 12 is closed. That is, the inner surface of the first cover 12 is not exposed to the outside environment while the first cover 12 is closed.

The display seating recess 129 may be disposed at the other end of the first cover 12. In this case, the display seating recess 129 may be formed in a shape corresponding to the display 20. When the device storage cover 11 is closed, the display 20 may seat in the display seating recess 129.

In the present embodiment, when the device storage cover 11 is closed, a portion corresponding to half of the display 20 may be seated in the display seating recess 129. Therefore, the display 20 may be easily disposed at the center of the device storage cover 11.

The display seating recess 129 and the display 20 may be provided with a magnet member, respectively. The display seating recess 129 and the display 20 may be fixed by the magnetic attraction of the magnet member. The device storage cover 11 may be opened when one or more of the first cover 12 and the second cover 13 are opened with a force greater than the attraction force of the magnet member.

The device storage body 10 may include at least one depression 109. The depression 109 may be a space into which the user's finger may be inserted in order to open the device storage cover 11. The depression 109 may be formed by recessing a portion of the device storage body 10.

The depression 109 may be formed in plural. A plurality of depressions 109 may be disposed on one side of the storage device body 10 to which the first cover 12 or the second cover 13 is coupled. The depression 109 may be formed on the side 10b, 10c of the device storage body 10. The depression 109 may be formed above the first side surface 10b or above the second side surface 10c or both. A depression 109 may be formed by recessing or cutting downward from the top of the first side surface 10b and/or the second side surface 10c.

The depression 109 may be formed to be connected to the first coupling rib 108. A user's finger inserted into the depression 109 and a force applied may open any one of the second coupling rib 121 and the third coupling rib 131 that are fitted into the first coupling rib 108.

The device storage body 10 may include a power connector 106. The power connector 106 may be connected to an electrical wire 9 for receiving and supplying power to the mask storage apparatus 1. The electrical wire 9 may include a wire terminal 9a, and the wire terminal 9a may be connected to the power connector 106. The electrical wire 9 may supply power supplied from an outside power source to the mask storage apparatus 1.

The device storage body 10 may include a connector installation groove 107. The connector installation groove 107 may be formed by recessing a portion of the device storage body 10. The power connector 106 may be located in the connector installation groove 107. In this embodiment, the connector installation groove 107 may be formed at the bottom surface of the device storage body 10, that is, at the bottom surface 10a of the device storage body 10. The connector installation groove 107 may be formed by recessing upward from the bottom of the bottom surface 10a of the device storage body 10. The connector installation groove 107 may prevent the wire terminal 9a connected to the power connector 106 from protruding out from the bottom surface 10a of the device storage body 10 or directly making contact with the ground.

The connector installation groove 107 may be provided with an air inlet or an air outlet to be described later. The air inlet or the air outlet may be an opening in which internal air inside the mask storage apparatus 1 communicates with external air outside of the mask storage apparatus 1.

According to one embodiment, some of the bottom surface 10a of the device storage body 10 may be spaced apart from the ground by a predetermined height H. A portion of the bottom surface 10a may be spaced upwardly from the ground. The bottom surface 10a may be formed in a convex shape protruding upward from both sides going toward the center. Therefore, a gap may be formed between a portion of the bottom surface 10a of the device storage body 10 and the ground.

The remaining part of the bottom surface 10a of the device storage body 10 may be formed for contact with the ground. The bottom surface 10a of the device storage body 10 may be formed in an arch shape and having end portions for being supported by the ground.

To summarize, both end portions of the bottom surface 10*a* may be supported by the ground, and the center of the bottom surface 10*a* may be spaced apart from the ground by a predetermined height H. The connector installation groove 107 may be formed on the bottom surface 10*a* spaced at a predetermined height H from the ground. Since the connection connector 106 and the wire terminal 9*a* are disposed at a position spaced apart from the ground, the connection connector 106 and the wire terminal 9*a* may be protected from foreign matter or moisture present on the ground.

The device storage body 10 may include a compartment. The compartment may be disposed inside the device storage body 10. The compartment may be disposed to protrude from the center in a vertical direction from an inner surface of the device storage body 10. The compartment may divide the accommodation space of the device storage body 10 into a first accommodation space 104 and a second accommodation space 105.

The first accommodation space 104 may be a space in which a part of the mask device 8 is accommodated. The second accommodation space 105 may be a space in which the remaining part of the mask device 8 is accommodated. The first accommodation space 104 may be a space formed in one side of the compartment and the first cover 12. The second accommodation space 105 may be a space formed between the other side of the compartment and the second cover 13.

The compartment may comprise a protrusion 16. The protrusion 16 may protrude from the bottom surface 10*a* and/or side surfaces 10*b* and 10*c* of the device storage body 10. The protrusion 16 extends upward from a portion of the bottom surface 10*a* and may be connected to the first side surface 10*b* and the second side surface 10*c*.

Alternatively, the protrusion 16 may protrude in the direction from the inner surface of the device storage body 10 towards the open surface of the device storage body 10. The protrusion 16 may extend in a direction from one side of the inner surface of the device storage body 10 towards the other side of the inner surface of the device storage body 10.

The protrusion 16 may be formed in a stepped shape on the inner surface of the device storage body 10. In this case, a seating surface on which the air module 18 and electronic components, to be described below, may be seated may be provided on an upper surface or an inner surface of the protrusion 16.

The compartment may further include an air module 18. The air module 18 may forcibly circulate the internal air of the device storage body 10. The air module 18 may suck the internal air of the accommodation space and discharge the sucked internal air back into the accommodation space. The air module 18 may suck air from the outside environment and discharge the sucked air into the accommodation space. The air module 18 may suck the internal air of the accommodation space and discharge the sucked air to the outside environment.

In the present embodiment, the air module 18 may be seated inside the protrusion 16. The protrusion 16 protrudes outward from the bottom surface 10*a* and side surfaces 10*b* and 10*c* to provide a predetermined seating surface or seating space internally. The air module 18 may be seated on the seating surface of the protrusion 16. In one embodiment, the air module 18 may be detachably seated on the seating surface of the protrusion 16.

The air module 18 may include a fan, a motor, and an air cover which covers the fan and the motor and includes one or more holes through which air passes through. The air module 18 may include a plurality of electronic components 102 and 103 disposed inside the air cover. The plurality of electronic components 102 and 103 may be disposed on a seating surface of the protrusion 16.

The compartment may further include a sterilization module 17. The sterilization module 17 may sterilize the mask device 8 stored in the accommodation space of the device storage body 10. In the present embodiment, the sterilization module 17 may be a sterilizing lamp for generating ultraviolet sterilizing light and a lamp cover covering the sterilizing lamp.

The sterilization module 17 may be disposed above the air module 18 and located under the mask device 8 to be stored in the accommodation space. That is, the sterilization module 17 may be disposed to be adjacent to the inner side of the mask device 8 to improve the sterilization of the mask device 8.

The sterilization module 17 may sterilize the mask device 8 stored in the first accommodating space 104 and the second accommodating space 105. A part of the mask device 8 sterilized by the sterilization module 17 may be one surface of the mask device 8 facing the user's nose and mouth. The configuration of the sterilization module 17 will be described in more detail below.

In the present embodiment, the compartment may be the protrusion 16 itself Alternatively, the compartment may be a configuration including the protrusion 16 and the air module 18. That is, the protrusion 16 may function as the compartment, and/or the air module 18 may function as the compartment.

Hereinafter, a process of storing the mask device 8 in the mask storage apparatus 1 will be described.

The user may wear the mask device 8 to be protected against germs, dust, and the like. After using the mask device 8, the user may store the mask device 8 in the mask storage apparatus 1. The user may open the device storage device 1 to access the device storage body 10 in order to store the mask device 8.

The first cover 12 and the second cover 13 may be opened by inserting a user's finger into the depression 109 provided in the device storage body 10. The first cover 12 and the second cover 13 are rotated by the first hinge 14 and the second hinge 15, and the accommodation space of the device storage body 10 may be exposed.

The mask device 8 may be stored in the accommodation space of the device storage body 10. A portion of the mask device 8 may be accommodated in the first accommodating space 104, and remaining portion of the mask device 8 may be accommodated in the second accommodating space 105. In addition, a part of the mask device 8 accommodated in the first accommodation space 104 and the second accommodation space 105 may be located above the compartment.

That is, the mask device 8 covers at least a portion of the compartment, and the inner side of the mask device 8 may extend over the protrusion 16 or the sterilization module 17. When the mask device 8 is stored in the accommodation space of the device storage body 10, the device storage body is closed by the device storage cover 11 and the mask device 8 may be stored in the mask storage apparatus 1.

When the device storage device body 10 is closed by the device storage cover 11, the storage device cover 11 may apply pressure in the direction towards the compartment where the mask device 8 is stored in the accommodation space of the device storage body 10. When the device storage cover 11 presses against the mask device 8 in the direction towards the compartment, the mask device 8 may be kept immobile in the mask storage apparatus 1, thus damage to the mask device 8 due to the movement of the mask storage apparatus 1 may be minimized.

Figure 7:
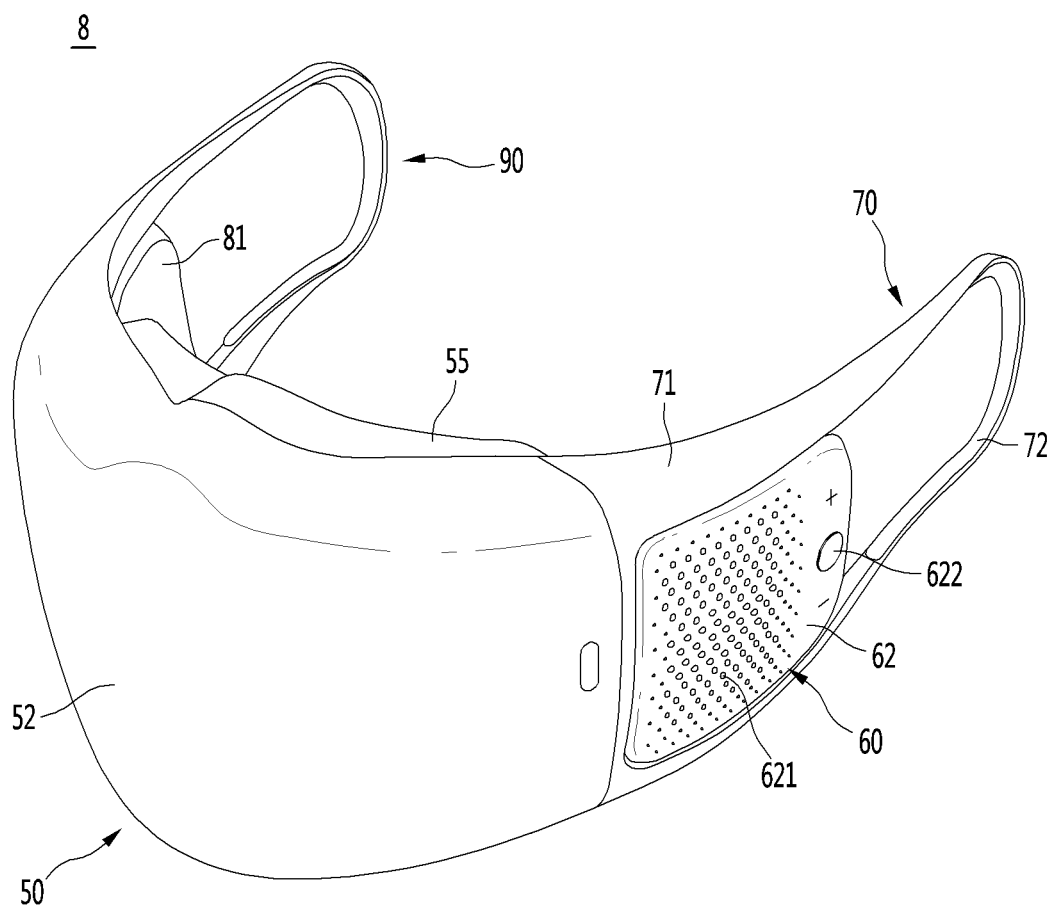
FIG. 7 is a perspective view of a mask device according to an embodiment of the present invention.
Figure 8:
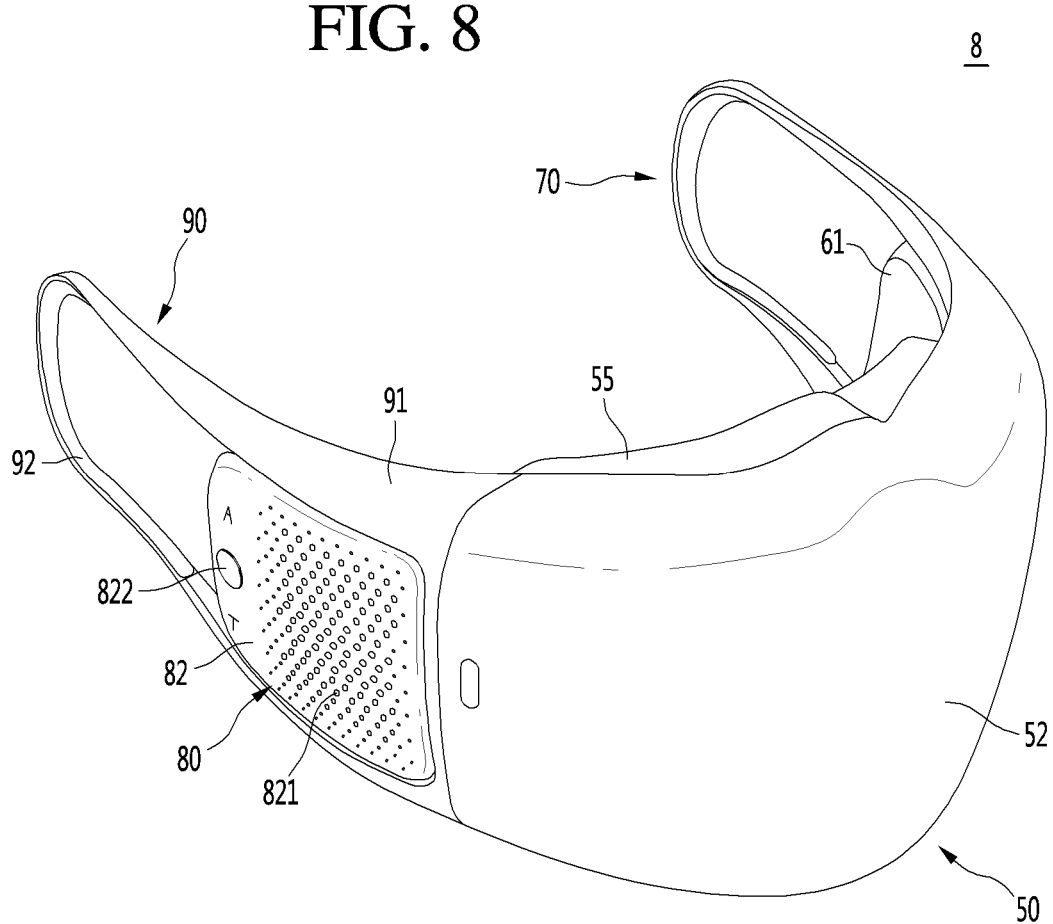
FIG. 8 is a perspective view of the mask device according to the embodiment of the present invention viewed from another direction.
Figure 9:
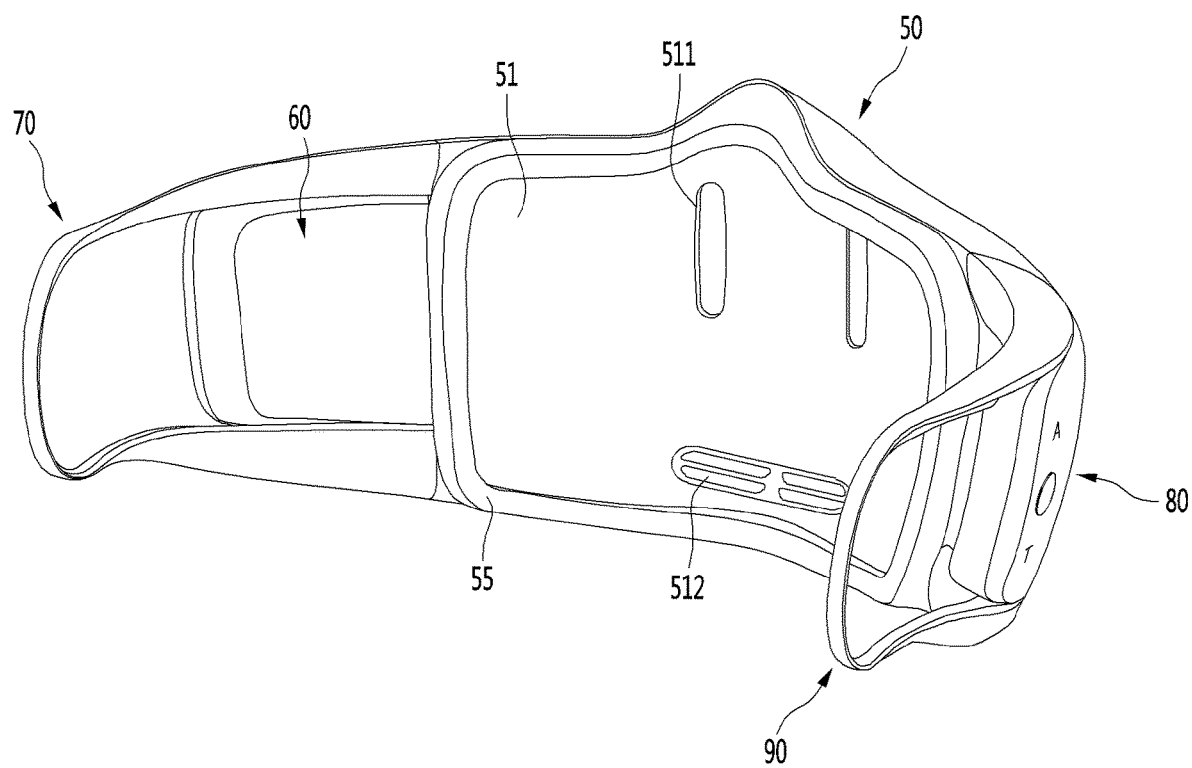
FIG. 9 is a rear perspective view of the mask device according to the embodiment of the present invention.

FIG. 7 is a perspective view of a mask device according to an embodiment of the present invention, FIG. 8 is a perspective view of the mask device according to the embodiment of the present invention viewed from another direction, and FIG. 9 is a rear perspective view of the mask device according to the embodiment of the present invention.

Referring to FIGS. 7 to 9, the mask device 8 according to the embodiment of the present invention may include a mask body 50. The mask body 50 may be in close contact with the face of the user. When the mask body 50 is in close contact with the face of the user, it may cover the mouth and nose of the user.

The mask body 50 may include a frame 51 and a front cover 52. The frame 51 and the front cover 52 may be detachably coupled to each other. The frame 51 may form part of the mask body 50. The front cover 52 may form the remaining part of the mask body 50.

A part of the mask body 50 may be disposed to be in a direction towards the nose and mouth of the user. The remaining part of the mask body 50 may be disposed to be in a direction towards the outside environment. The frame 51 may be disposed to be in front of the user's nose and mouth, and may form a space through which air flowing into the user's nose and mouth passes. The front cover 52 may be disposed to be in a direction toward the outside environment and may form an outer appearance of the mask body 50.

The frame 51 may include an inlet 511 and an outlet 512. The inlet 511 may be an opening for supplying air filtered by a first air cleaner 60 and a second air cleaner 80, to be described later, in a direction towards the user's nose and mouth.

The outlet 512 may be an opening for discharging air discharged from the user's nose and mouth to the outside environment. In the present embodiment, the inlet 511 may be located corresponding to the front of the user's nose. The outlet 512 may be located corresponding to the front of the user's mouth. The position arrangement of the inlet 511 and the outlet 512 may be changed in various ways depending on the situation.

In the present embodiment, the inlet 511 may be formed with an opening larger than the outlet 512 to facilitate the inflow of filtered air. The size of the inlet 511 and the outlet 512 may be changed in various ways depending on the situation. Air flowing in through the inlet 511 and air flowing out through the outlet 512 may flow separated from each other in the mask body 50.

The mask body 50 may include a first fixing part (not shown) and a second fixing part (not shown). The first fixing part and the second fixing part may allow the first air cleaner 60 and the second air cleaner 80, to be described later, to be fixed to the mask body 50.

In the present embodiment, the first fixing part may be disposed on the left side of the mask body 50, and the second fixing part may be disposed on the right side of the mask body 50. Positions of the first fixing part and the second fixing part may be variously changed according to the situation.

The first fixing part and the second fixing part may be disposed between the front cover 52 and the frame 51. In the present embodiment, a portion of the first fixing part and the second fixing part may be fixed to the front cover 52. The remaining part of the first fixing part and the second fixing part may be fixed to the frame 51.

For example, the first fixing part may be inserted and fixed in an inner direction of the mask body 50 at the left end of the mask body 50. The second fixing part may be inserted and fixed in an inner direction of the mask body 50 at the right end of the mask body 50. That is, a fixing part mounting groove may be formed between the frame 51 and the front cover 52 to allow the first fixing part and the second fixing part to be seated.

The mask body 50 may include a gasket 55. The gasket 55 may be fixed to the frame 51. The gasket 55 may interpose between the frame 51 and the user's face when the mask body 50 is in close contact with the user's face.

The gasket 55 may be made of a material, for example, soft rubber, that deforms into a shape corresponding to the face of the user when the mask body 50 is in contact with the user's face. That is, the gasket 55 may modify to correspond to the face of the user, thereby minimizing the occurrence of a gap between the frame 51 and the face of the user.

The mask device 8 may include a first air cleaner 60 and a second air cleaner 80. The first air cleaner 60 and the second air cleaner 80 may be disposed on both sides of the mask body 50, respectively. In the present embodiment, the first air cleaner 60 may be disposed on the left side of the mask body 50, and the second air cleaner 80 may be disposed on the right side of the mask body 50.

The first air cleaner 60 and the second air cleaner 80 may be fixed to the first fixing part and the second fixing part of the mask body 50, respectively. The first air cleaner 60 and the second air cleaner 80 may move relative to the first fixing part and the second fixing part.

For example, the first air cleaner 60 may be folded with respect to the first fixing part, and the second air cleaner 80 may be folded with respect to the second fixing part have. In the present embodiment, the first air cleaner 60 and the second air cleaner 80 are described as being folded relative to the first fixing part and the second fixing part, but it may also be understood as being rotatable. When the first air cleaner 60 and the second air cleaner 80 are folded with respect to the mask body 50, the mask device 8 may be easily stored.

In addition, when the first air cleaner 60 and the second air cleaner 80 are folded in the direction toward the frame 51 of the mask device 8, the first air cleaner 60 and the second air cleaner 80 folds to close at least a part of the space where the user's nose and mouth may be located, thereby minimizing the introduction of foreign substances into the space where the user's nose and mouth may be located.

The first air cleaner 60 and the second air cleaner 80 may suck air from the outside environment and filter the sucked air. The filtered air is introduced into the mask body 50 and may be supplied to the nose and/or mouth of the user through the inlet 511. Since the air filtered by each of the first air cleaner 60 and the second air cleaner 80 is supplied to the inlet 511, the user's breathing may be smoothly performed.

The first air cleaner 60 may include a first cleaner body 61 and a first cleaner cover 62. The first cleaner body 61 and the first cleaner cover 62 may be detachably coupled to each other. When the first cleaner cover 62 is separated from the first cleaner body 61, components in the first cleaner body 61 may be accessed.

The first cleaner body 61 may have a space in which a plurality of components are accommodated. For instance, the first fan module and the first filter module may be disposed in the first cleaner body 61. The first fan module may generate a suction force for sucking outside air.

The first filter module may filter foreign matters from the sucked air. The first filter module may be disposed upstream of the first fan module based on a flow direction of air. Alternatively, the first filter module may be disposed downstream of the first fan module based on the flow direction of air, but it is preferable to be disposed upstream.

A battery may be disposed inside the first cleaner body 61. The battery may supply power for operating the first air cleaner 60. In addition, the battery may supply power for operating the second air cleaner 80 to be described later. The battery may be connected to the first air cleaner 60 and the second air cleaner 80 by an electrical wire.

In the present embodiment, the first air cleaner 60 and the second air cleaner 80 may be powered by one battery. When the battery is disposed inside one of the first air cleaner 60 and the second air cleaner 80, a circuit board for operating the first air cleaner 60 and the second air cleaner 80 may be disposed inside the other one of the first air cleaner 60 and the second air cleaner 80. That is, the battery and the circuit board, which may correspond to the weight of the battery, may be disposed in the respective first air cleaner 60 and second air cleaner 80, so that the load may be evenly balanced in the mask device 8.

The first cleaner cover 62 may include a first suction port 621 and a first switch 622. The first suction port 621 may be an opening through which air from the outside environment is sucked in. Air passing through the first suction port 621 may pass through the inlet 511. The first suction port 621 may be formed with a plurality of openings. The first switch 622 may be an operation switch for operating the first air cleaner 60. In the present embodiment, the first switch 622 may operate as an operation switch for operating the second air cleaner 80.

The second air cleaner 80 may include a second cleaner body 81 and a second cleaner cover 82. The second cleaner body 81 and the second cleaner cover 82 may be detachably coupled to each other. When the second cleaner cover 82 is separated from the second cleaner body 81, components in the second cleaner body 81 may be accessed.

The second cleaner body 81 may have a space in which a plurality of components are accommodated. For instance, the second fan module and the second filter module may be disposed in the second cleaner body 81. The second fan module may generate a suction force for sucking outside air. The second filter module may filter foreign matters from the sucked air. The second filter module may be disposed upstream of the second fan module based on the flow direction of air. Alternatively, the second filter module may be disposed downstream of the second fan module based on the flow direction of air, but it is preferable to be disposed upstream.

A circuit board may be disposed in the second cleaner body 81. The circuit board may control the operation of one or more of the first air cleaner 60 and the second air cleaner 80. The circuit board may be connected to at least one of the first air cleaner 60 and the second air cleaner 80 by an electrical wire. In the present embodiment, both the first air cleaner 60 and the second air cleaner 80 may be controlled by the circuit board. The circuit board may be provided in plural. The plurality of circuit boards may include a first circuit board for controlling the first air cleaner 60 and a second circuit board for controlling the second air cleaner 80.

The second cleaner cover 82 may include a second suction port 821 and a second switch 822. The second suction port 821 may be an opening through which air from the outside environment is sucked in. Air passing through the second suction port 821 may pass through the inlet 511. The second suction port 821 may be formed with a plurality of openings. The second switch 822 may be an operation switch for operating the second air cleaner 80. In addition, the second switch 822 may operate as an operation switch for operating the first air cleaner 60. This is where the first operation switch 622 is not provided. In the event the first operation switch 622 is provided, the second operation switch 822 may not be needed if the first operation switch 622 also operates as an operation switch for operating the second air cleaner 80.

The mask device 8 may include a first ear catching part 70 and a second ear catching part 90. The first ear catching part 70 and the second ear catching part 90 may be detachably mounted to the first air cleaner 60 and the second air cleaner 80. The first ear catching part 70 may be mounted to the first air cleaner 60, and the second ear catching part 90 may be mounted to the second air cleaner 80.

The first ear catching part 70 may be fixed to the left ear of the user, and the second ear catching part 90 may be fixed to the right ear of the user. With the first air cleaner 60 and the second air cleaner 80 fixed to the mask body 50, the first ear catcher 70 and the second ear catcher 90 allows the user to fix the mask body 50 to the face of the user.

The first ear catching part 70 may include a first hook body 71. The first hook body 71 may be formed to be fixed to the user's ear. For example, the first hook body 71 may be provided in a string shape to be fixed to a user's ear.

In this case, one side of the first hook body 71 may be fixed to the first air cleaner 60, and the other side of the first hook body 71 may be fixed to the ear of the user. Between the first air cleaner 60 and the user's ear, the first hook body 71 may be stretchable and contracts so that the mask body 50 may be in close contact with the face of the user.

The first hook body 71 may include a first contact portion 72. The first contact portion 72 may be a part which contacts the user's ear when the first hook body 71 is mounted on the user's ear. The first contact portion 72 may be in contact with the user's ear to minimize the pressure applied by the first hook body 71 to the user's ear. The first contact portion 72 may be disposed to intervene between a user's ear and an inner surface of the first hook body 71. The first contact portion 72 may be provided on an inner surface of the first hook body 71 to which a user's ear may contact.

The second ear catching part 90 may include a second hook body 91. The second hook body 91 may be formed to be fixed to the user's ear. For example, the second hook body 91 may be provided in a string shape to be fixed to the user's ear.

In this case, one side of the second hook body 91 may be fixed to the second air cleaner 80, and the other side of the second hook body 91 may be fixed to the user's ear. Between the second air cleaner 80 and the user's ear, the second hook body 91 may be stretchable and contracts so that the mask body 50 is in close contact with the face of the user.

The second hook body 91 may include a second contact portion 92. The second contact portion 92 may be a part that contacts the user's ear when the second hook body 91 is mounted on the user's ear. The second contact portion 92 may be in contact with the user's ear to minimize the pressure applied by the second hook body 91 to the user's ear. The second contact portion 92 may be disposed to intervene between a user's ear and an inner surface of the second hook body 91. The second contact portion 92 may be provided on an inner surface of the second hook body 91 to which the user's ear may contact.

In the present embodiment, the first air cleaner 60 and the second air cleaner 80 may be folded with respect to the mask body 50. When the mask device 8 is used, the first air cleaner 60 and the second air cleaner 80 may be unfolded to be fixed to both sides of the mask body 50. The user may wear the mask device 8 while the first air cleaner 60 and the second air cleaner 80 are fixed to both sides of the mask body 50 (that is, unfolded).

When the user is not using the mask device 8, the first air cleaner 60 and the second air cleaner 80 may be folded with respect to the mask body 50. When the first air cleaner 60 and the second air cleaner 80 are folded toward the frame 51 of the mask body 50, the area where the frame 51 of the mask body 50 is exposed to the outside environment may be minimized. That is, the frame 51 portion where the user's nose and mouth may be located may be prevented from being exposed to the outside environment and being contaminated.

The first air cleaner 60 and the second air cleaner 80 may be folded with respect to the mask body 50, and the mask device 8 may be stored inside the mask storage apparatus 1.

Figure 10:
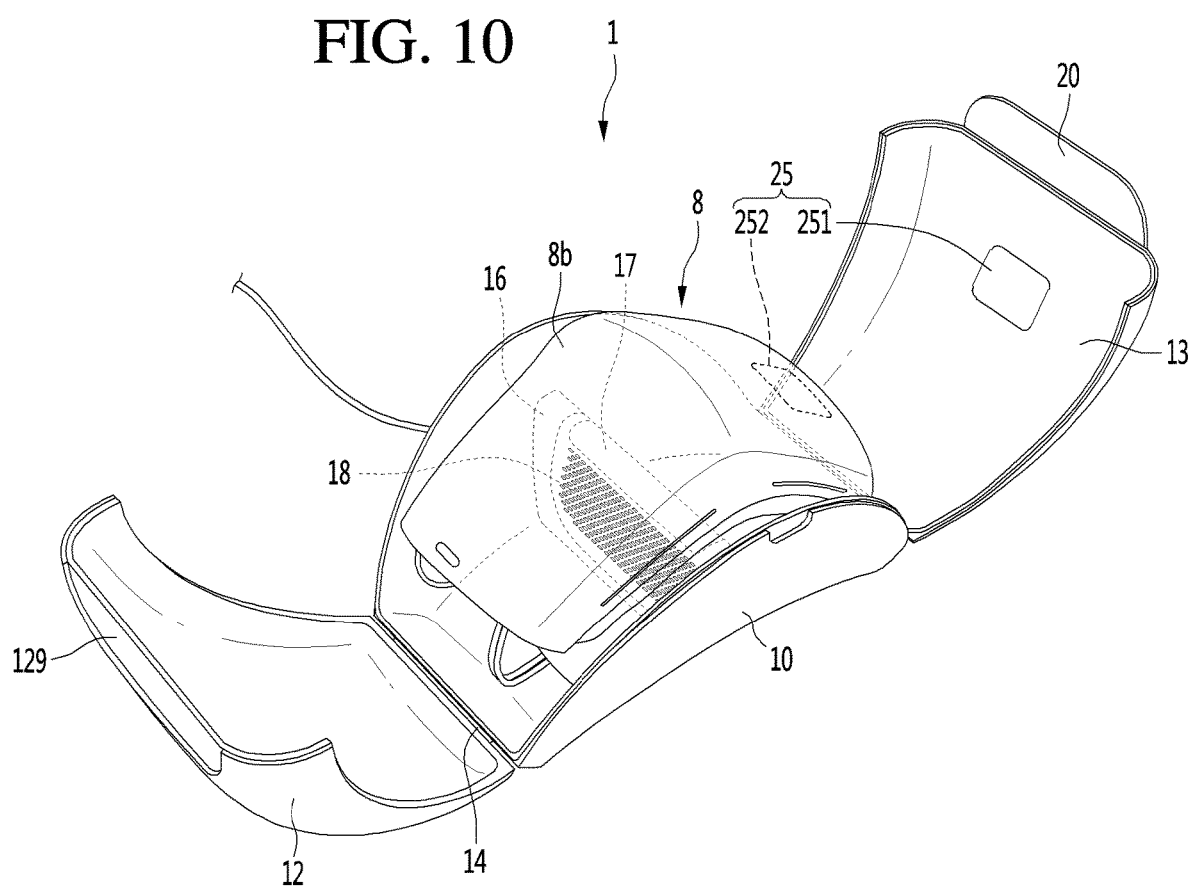
FIG. 10 is a view showing a sterilization of the mask device in the mask storage apparatus according to the first embodiment of the present invention.
Figure 11:
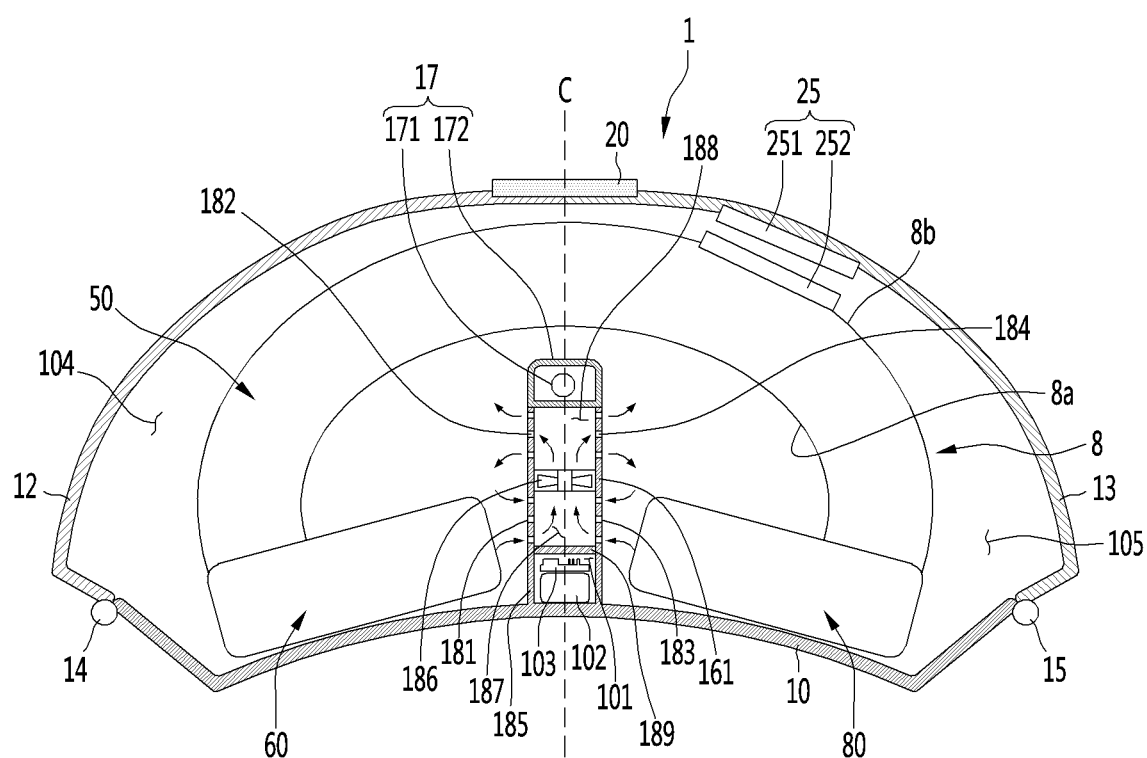
FIG. 11 is a cross-sectional view showing an internal view of the mask storage apparatus according to the first embodiment of the present invention in which a mask device is stored.

FIG. 10 is a view showing a sterilization of the mask device 8 in the mask storage apparatus 1 according to the first embodiment of the present invention, and FIG. 11 is a cross-sectional view showing an internal view of the mask storage apparatus 1 according to the first embodiment of the present invention in which the mask device 8 is stored.

Referring to FIGS. 10 and 11, the mask device 8 is stored inside the mask storage apparatus 1. The mask device 8 stored in the mask storage apparatus 1 may be sterilized by the sterilization module 17. In addition, the mask device 8 stored in the mask storage apparatus 1 may be dried by the air module 18.

The mask device 8 may include a first surface 8a that may cover a user's nose and mouth, and a second surface 8b that may be exposed to an outside environment. The mask storage apparatus 1 may provide for the first surface 8a of the mask device 8 to be cleaned.

The sterilization module 17 of the mask storage apparatus 1 may be positioned inside the mask device 8 when stored inside the mask storage apparatus 1. The sterilization module 17 may be arranged adjacent to or facing the first surface 8a of the mask device 8. The second surface 8b of the mask device 8 may face the first cover 12 and the second cover 13 of the mask storage apparatus 1.

The sterilization module 17 may sterilize the first surface 8a of the mask device 8. For example, the sterilizing module 17 may include a sterilizing lamp 171 for generating sterilizing light and a lamp cover 172 covering the sterilizing lamp 171. The sterilizing lamp 171 may be provided as an ultraviolet lamp for generating germicidal light. The lamp cover 172 may be made of a material having excellent light transmittance so that the light generated from the germicidal lamp 171 may be effectively irradiated to the first surface 8a of the mask device 8.

The sterilization module 17 may be provided at an upper portion of the protrusion 16. The sterilization module 17 may be disposed above the air module 18. When the sterilization module 17 is located above the protrusion 16, the sterilization module 17 may be located close to the first surface 8a of the mask device 8.

The air module 18 may dry the first surface 8a and/or the second surface 8b of the mask device 8. The air module 18 may include an air cover 185 including air inlets 181 and 183 through which air is sucked in, and air outlets 182 and 184 through which the suctioned air is discharged.

The air cover 185 may be located at the protrusion 16. The air cover 185 may be seated on a seating surface formed by the protrusion 16. The air cover 185 may be attached into a space formed by the protrusion 16 and may be detachable from the protrusion 16. An air passage 188 is formed in the air cover 185 to connect the air inlets 181 and 183 and the air outlets 182 and 184.

The air module 18 may include a fan module 186 for forcibly flowing air. The air module 18 may be disposed in the air passage 188.

The air inlets 181 and 183 may include a first air inlet 181 for sucking air in the first accommodation space 104 and a second air inlet 183 for sucking air in the second accommodation space 105. The first air inlet 181 is disposed toward the first accommodation space 104, and the second air inlet 183 is disposed toward the second accommodation space 105. That is, the first air inlet 181 and the second air inlet 183 may face in opposite directions.

The air outlets 182 and 184 may include a first air outlet 182 for discharging air into the first accommodation space 104 and a second air outlet 184 for discharging air to the second accommodation space 105. The first air outlet 182 is disposed toward the first accommodation space 104, and the second air outlet 184 is disposed toward the second accommodation space 105. That is, the first air outlet 182 and the second air outlet 184 may face in opposite directions.

In the present embodiment, the first air inlet 181, the second air inlet 183, the first air outlet 182, and the second air outlet 184 may be formed to be opened in the air cover 185. In addition, the air inlets 181 and 183 and the air outlets 182 and 184 may communicate with the air passage 188.

With such a configuration, when the fan module 186 is operated, the first air inlet 181 and the second air inlet 183 may suck the air in the first accommodation space 104 and the second accommodation space 105, respectively. The sucked air may pass through the first air outlet 182 and the second air outlet 184 and then be discharged into the first accommodation space 104 and the second accommodation space 105, respectively.

In the present embodiment, the air outlets 182 and 184 may be disposed to be close to the sterilization module 17, and the air inlets 181 and 183 may be disposed to be close to the bottom surface 10a of the device storage body 10.

For example, the air inlets 181 and 183 may be positioned at a lower portion of the air cover 185, and the air outlets 182 and 184 may be positioned at an upper portion of the air cover 185. The air outlets 182 and 184 may be located above the air inlets 181 and 183.

The fan module 186 may be positioned in the air passage 188 between the air inlets 181 and 183 and the air outlets 182 and 184. Accordingly, the air in the accommodation spaces 104 and 105 may be sucked in from the lower portion of the air cover 185 and then discharged from the upper portion of the air cover 185. That is, since the sucked air may be discharged in the direction toward the first surface 8a of the mask device 8, the first surface 8a of the mask device 8 may be effectively dried.

While a preferred embodiment has been described, the fan module 186 may be operated in a direction opposite to the fan module 186 described above. In this instance, the air may be sucked in from the upper portion of the air cover 185 and may be discharged to the lower portion of the air cover 185.

The air module 18 may further include an air filter. The air filter may be disposed upstream of the fan module 186 based on the air flow direction. The air filter may be formed so as to replace the air cover 185. In this case, when the fan module 186 is operated, the internal air of the mask storage apparatus 1 may be filtered as the air circulates in the first accommodation space 104 and the second accommodation space 105.

The mask storage apparatus 1 may further include an installation space 101 in which electronic components may be accommodated. The installation space 101 may be formed in the compartment. The installation space 101 may be formed in the air cover 185.

For example, when the air cover 185 is seated on the protrusion 16, the installation space 101 may be provided below the air cover 185. The air cover 185 may be provided with a partition plate 189 that divides the internal space of the air cover 185 into the air passage 188 and the installation space 101.

The partition plate 189 may be horizontally disposed inside the air cover 185. The partition plate 189 may be disposed below the air inlets 181 and 183, and may facilitate in the air flow.

The installation space 101 may store a battery 102 for supplying power to the mask storage apparatus 1 and a circuit board 103 for controlling the operation of the mask storage apparatus 1. The battery may be a disposable battery or may be a rechargable battery. If the battery is a rechargable battery, the battery may be charged by receiving power through the electrical wire 9. The battery 102 may supply power to the fan module 186 or supply power to the display 20. In addition, the battery 102 may supply power to a wireless charger 25 to be described below. The circuit board 103 may control the operation of the fan module 186, the operation of the display 20, and the like.

The mask storage apparatus 1 may include a wireless charger 25. The wireless charger 25 may be used for supplying power to the mask device 8 stored in the mask storage apparatus 1. The wireless charger 25 may include a power transmitter 251 for wirelessly transmitting power, and a power receiver 252 for receiving the transmitted power.

In the present embodiment, the power transmitter 251 may be provided at the device storage cover 11, and the power receiver 252 may be provided at the mask device 8. The power transmitter 251 may be disposed on an inner surface of at least one of the first cover 12 and the second cover 13. The power receiver 252 may be disposed at the mask body 50 of the mask device 8. The power receiver 252 may be disposed on the second surface 8b of the mask device 8. The power transmitter 251 and the power receiver 252 may be disposed at positions corresponding to each other.

When the device storage cover 11 closes on the device storage body 10, the power transmitter 251 and the power receiver 252 may be facing each other. The power transmitter 251 may wirelessly transmit power and the power receiver 252 may wireless receive power using a magnetic resonance method or a magnetic induction method. Power transmitted from the power transmitter 251 to the power receiver 252 may be supplied to the battery 102. Alternatively, the power may be supplied by an external power source through the electrical wire 9.

The power receiver 252 may receive power wirelessly from the power transmitter 251. The power delivered to the power receiver 252 may be used for the operation of the mask device 8. For example, the mask device 8 may include a battery, and the power delivered to the power receiver 252 may charge the battery. That is, when the mask device 8 is stored in the mask storage apparatus 1, the battery provided in the mask device 8 may be charged.

Figure 12:
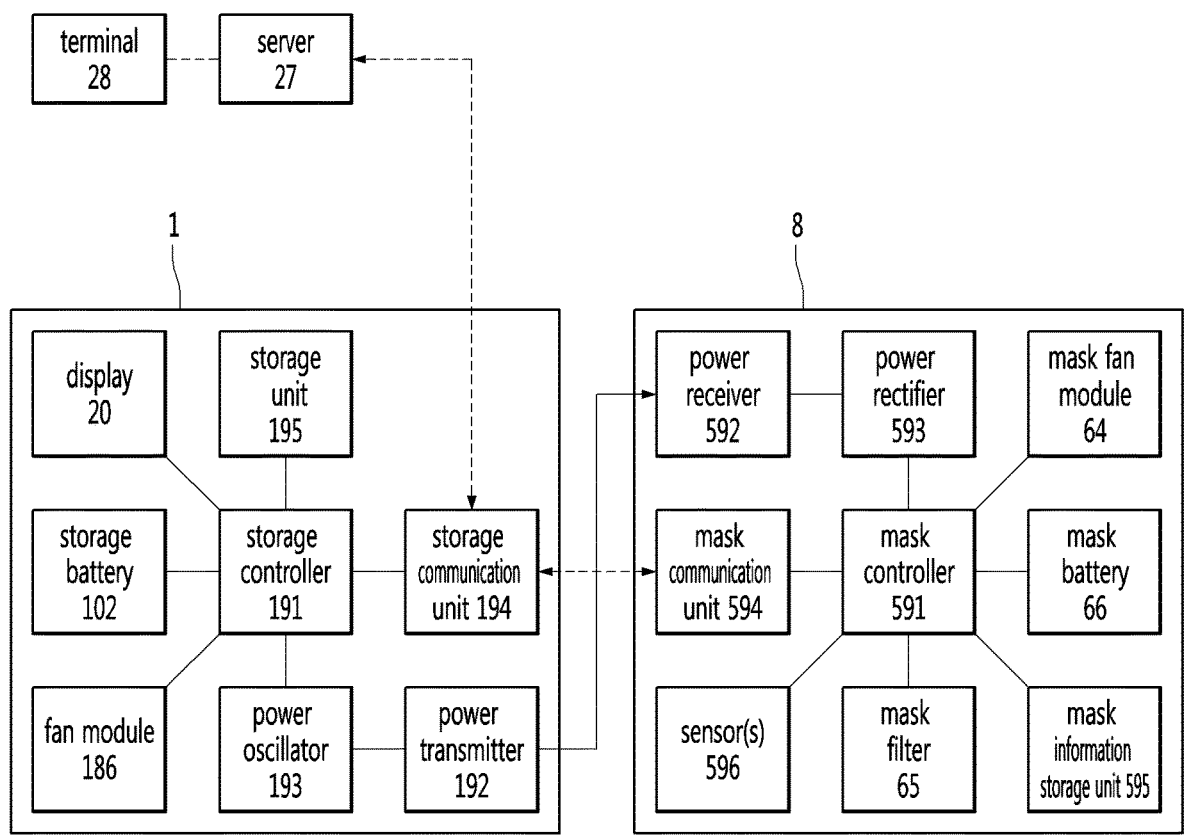
FIG. 12 is a block diagram showing a configuration of a mask storage apparatus and a mask device according to the first embodiment of the present invention.

FIG. 12 is a block diagram showing a configuration of a mask storage apparatus 1 and a mask device 8 according to the first embodiment of the present invention.

Referring to FIG. 12, the mask device 8 may be stored in the mask storage apparatus 1 according to the embodiment of the present invention. The mask storage apparatus 1 may charge, dry, and sterilize the mask device 8. The mask device 8 may be charged by the mask storage apparatus 1 and may be mounted on and operated on a face of a user.

The mask device 8 may include a mask controller 591. For example, the mask controller 591 may be a microprocessor, a digital signal processor, an integrated circuit, an electrical logical circuit, and the like. The mask controller 591 may control the operation of the mask device 8. The mask controller 591 may control the operation of the mask fan module 186 of the mask device 8. In the present embodiment, the mask fan module 186 may include a first fan module and a second fan module included in the mask device 8. The mask controller 591 may control operations of all components included in the mask device 8.

The mask device 8 may include a power receiver 592. The power receiver 592 may receive power wirelessly transmitted from the power transmitter 192 of the mask storage apparatus 1. The power receiver 592 may be changed in configuration according to the wireless power supply method. For example, the power receiver 592 may be provided as a coil, an antenna, a resonator, or the like. Operation of the power receiver 592 may be controlled by the mask controller 591.

The mask device 8 may include a power rectifier 593. The power rectifier 593 may rectify the power wirelessly received by the power receiver 592. The power rectifier 593 may rectify the power whose frequency is changed into a power source that may be used in the mask device 8. The power rectified by the power rectifier 593 may be used to power the mask device 8.

The mask device 8 may include a mask battery 66 for operating the mask device 8. The mask device 8 may be driven with the power stored in the mask battery 66. The mask controller 591 may check the state of the mask battery 66 and control the operation of the mask device 8 according to the state of the mask battery 66.

The mask battery 66 may be charged with the power supplied by the power receiver 592 and the power rectifier 593. The mask device 8 may include a separate charging connector for charging the mask battery 66, and a power cable may be connected to the charging connector to supply power.

The mask device 8 may include a mask filter 65. The mask filter 65 may filter the air supplied to the user by the mask device 8. The mask filter 65 may include a first filter and a second filter included in the first air cleaner 60 and the second air cleaner 80, respectively.

The mask device 8 may include a mask communication unit 594. The mask communication unit may be an electrical circuit that transmits and/or receives signals. The mask communication unit 594 may transmit and/or receive a plurality of information. In the present embodiment, the mask communication unit 594 may receive information from the mask storage device 1. For example, the information may include operation information of the mask device 8, operation information of the mask storage apparatus 1, and the like.

The mask communication unit 594 may transmit information to the mask storage apparatus 1. For example, the information may include operation information, state information, environment information, measured information, and the like of the mask device 8. The mask communication unit 594 may be controlled by the mask controller 591.

The mask device 8 may include a mask information storage unit 595. The mask information storage unit 595 may be provided as a memory such as a semiconductor memory, for example. The mask information storage unit 595 may store various information. The mask controller 591 may control the operation of the mask device 8 based on information stored in the mask information storage unit 595. The information may include control information for controlling the configuration of the mask device 8, frequency information transmitted from the power transmitter 192 of the mask storage apparatus 1, surrounding environment information of the mask device 8, state information of the mask device 8, operation information transmitted from the mask storage apparatus 1, and the like. These are examples, and the mask information storage unit 595 may store various information according to the needs of the mask device 8.

The mask device 8 may include one or more sensors 596. The one or more sensors 596 may detect a state of the mask device 8 and generate various information. The one or more sensors 596 may detect an external environmental state of the mask device 8 and generate various information. The one or more sensors 596 may detect a state of the mask filter module 65. The one or more sensors 596 may detect a state of air external to the mask device 8. Information generated by the one or more sensors 596 may be stored in the mask information storage unit 595. The mask device 8 may operate based on information detected by the one or more sensors 596. These are examples, and the one or more sensors 596 may detect and provide various information according to the needs of the mask device 8.

For example, the operation of the mask device 8 is controlled by the mask controller 591, and may detect information about the state of the mask device 8 and the environmental state through the one or more sensors 596. The mask device 8 may transmit and receive information to and from the mask storage apparatus 1 through the mask communication unit 594, and operate in conjunction with each other. The mask storage apparatus 1 may determine the state of the mask device 8 through the transmitted information, and perform an operation for managing the mask device 8 based on the transmitted information.

The mask storage apparatus 1 may include a storage controller 191. The storage controller 191 may be a microprocessor, a digital signal processor, an integrated circuit, an electrical logical circuit, and the like. The storage controller 191 controls the operation of the mask storage apparatus 1. The storage controller 191 may control an operation of the fan module 186 of the mask storage apparatus 1. The storage controller 191 may control the operation of the display 20. The storage controller 191 may control the operation of all components included in the mask storage apparatus 1.

The mask storage device 1 may include a power transmitter 192. The power transmitter 192 may receive power from the storage battery 102. The power transmitter 192 may transmit power wirelessly to the power receiver 592 included in the mask device 8. The power transmitter 192 may vary in configuration depending on a wireless power supply method. For example, the power transmitter 192 may be provided as a coil, an antenna, a resonator, or the like.

The mask storage apparatus 1 may include a power oscillator 193. The power oscillator 193 may change the frequency of the power wirelessly transmitted from the power transmitter 192. In this case, the frequency changed by the power oscillator 193 may be a resonance frequency. Power changed to a specific frequency by the power oscillator 193 may be transmitted from the power transmitter 192. The storage controller 191 may control the power oscillator 193 to transmit power changed to a specific frequency to the power receiver 592. The power oscillator 193 may include a power amplifier.

The mask storage apparatus 1 may include a storage communication unit 194. The storage communication unit may be an electrical circuit that transmits and/or receives signals. The storage communication unit 194 may transmit or receive various information. The storage communication unit 194 may transmit or receive various information from the mask device 8. For example, the information may include operation information, state information, environment information, measured information, and the like from or to the mask device 8.

The storage communication unit 194 may transmit or receive various information to/from a server 27 or a terminal 28. For example, the information may include operation information of the mask storage apparatus 1 and information received from the mask device 8. The storage communication unit 194 may be controlled by the storage controller 191.

The mask storage apparatus 1 may include a storage unit 195. The storage unit 195 may be provided as a memory, such as a semiconductor memory, for example. The storage unit 195 may store various information. The storage controller 191 may control the operation of the mask storage apparatus 1 based on the information stored in the storage unit 195. The information may include information for controlling the configuration of the mask storage apparatus 1, information transmitted from the mask device 8, frequency information of power wirelessly transmitted from the power transmitter 192, and the like.

In the present embodiment, the mask storage apparatus 1 may transmit or receive various information to/from the server 27 or the terminal 28 by using the storage communication unit 194. When information is transmitted to the server 27, the user may access the server 27 using the terminal 28 and check the transmitted information with the terminal 28. When information is transmitted to the terminal 28, the user may quickly check the information using the terminal 28.

The mask storage apparatus 1 may receive information on an operation from the server 27 or the terminal 28. The mask storage apparatus 1 may be operated based on information received from the server 27 or the terminal 28. The user may check the states of the mask device 8 and the mask storage apparatus 1 using the terminal 28. The user may input control information for controlling the operation of the mask device 8 and the mask storage apparatus 1 using the terminal 28. The mask device 8 and the mask storage apparatus 1 may operate based on control information transmitted from the terminal 28.

Figure 13:
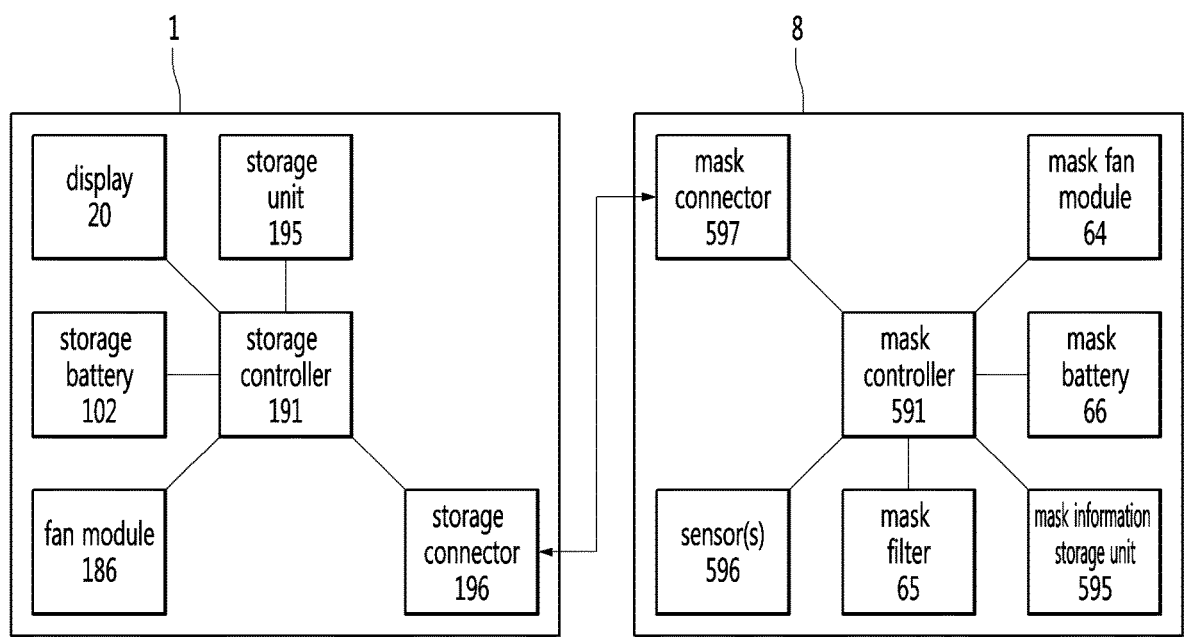
FIG. 13 is a block diagram showing a configuration of a mask storage apparatus and a mask device according to a second embodiment of the present invention.

FIG. 13 is a block diagram showing a configuration of a mask storage apparatus 1 and a mask device 8 according to a second embodiment of the present invention.

Descriptions of similar components and operations of the first embodiment that may be in the second embodiment may be omitted, and the characteristic parts of the second embodiment may be described, in conjunction with the similar components and operations of the first embodiment.

Referring to FIG. 13, the mask device 8 according to the embodiment of the present invention may include a mask fan module 64, a mask filter 65, a mask battery 66, a mask controller 591, a mask information storage unit 595, one or more sensors 596 and mask connector 597.

Since the mask fan module 64, the mask filter 65, the mask battery 66, the mask information storage unit 595, and the one or more sensors 596 are the same or similar to those of the first embodiment described above, a detailed description thereof will be omitted.

The mask device 8 according to the present embodiment may be stored inside the mask storage apparatus 1. When the mask device 8 is stored in the mask storage apparatus 1, the mask device 8 may be electrically connected physically to the mask storage apparatus 1.

The mask device 8 and the mask storage apparatus 1 may be connected by a connector. That is, when the mask device 8 is stored inside the mask storage apparatus 1, the mask device 8 and the mask storage apparatus 1 may be electrically connected by the connector. The mask device 8 and the mask storage apparatus 1 may transmit and receive various information and/or share power through the connector.

The configuration where the mask device 8 includes a mask connector 597 is described below.

The mask connector 597 may be provided in the mask device 8. For example, the mask connector 597 may be exposed to from the outer surface of the mask device 8. The mask connector 597 may be a connector for receiving power from the mask storage apparatus 1 and/or transmitting/receiving information. The mask device 8 may be electrically connected to the mask storage apparatus 1 through the mask connector 597.

The mask storage apparatus 1 may include a storage connector 196. The storage connector 196 may be provided on an inner surface of the mask storage apparatus 1. The storage connector 196 may be disposed at a position corresponding to the mask connector 597. The storage connector 196 may be electrically connected to the mask connector 597.

In the present embodiment, when the storage device cover 11 covers the mask body 50 while the mask device 8 is stored inside the mask storage apparatus 1, the mask connector 597 and the storage connector 196 may connect to each other. For example, the mask connector 597 may be disposed on one surface of the first air cleaner 60 or the second air cleaner 80 of the mask device 8. The storage connector 196 may be disposed on an inner surface of the mask storage apparatus 1 facing the mask connector 597.

According to this configuration, when the mask device 8 is stored in the mask storage apparatus 1, the mask connector 597 and the storage connector 196 may operate with respect to each other. Since the mask connector 597 and the storage connector 196 are directly or physically connected (as opposed to being connected wirelessly), losses that may occur in power or information transmission may be reduced. That is, since the mask connector 597 and the storage connector 196 are connected by wire or physically connected, the power and the information transmission/reception rate may be improved.

Figure 14:
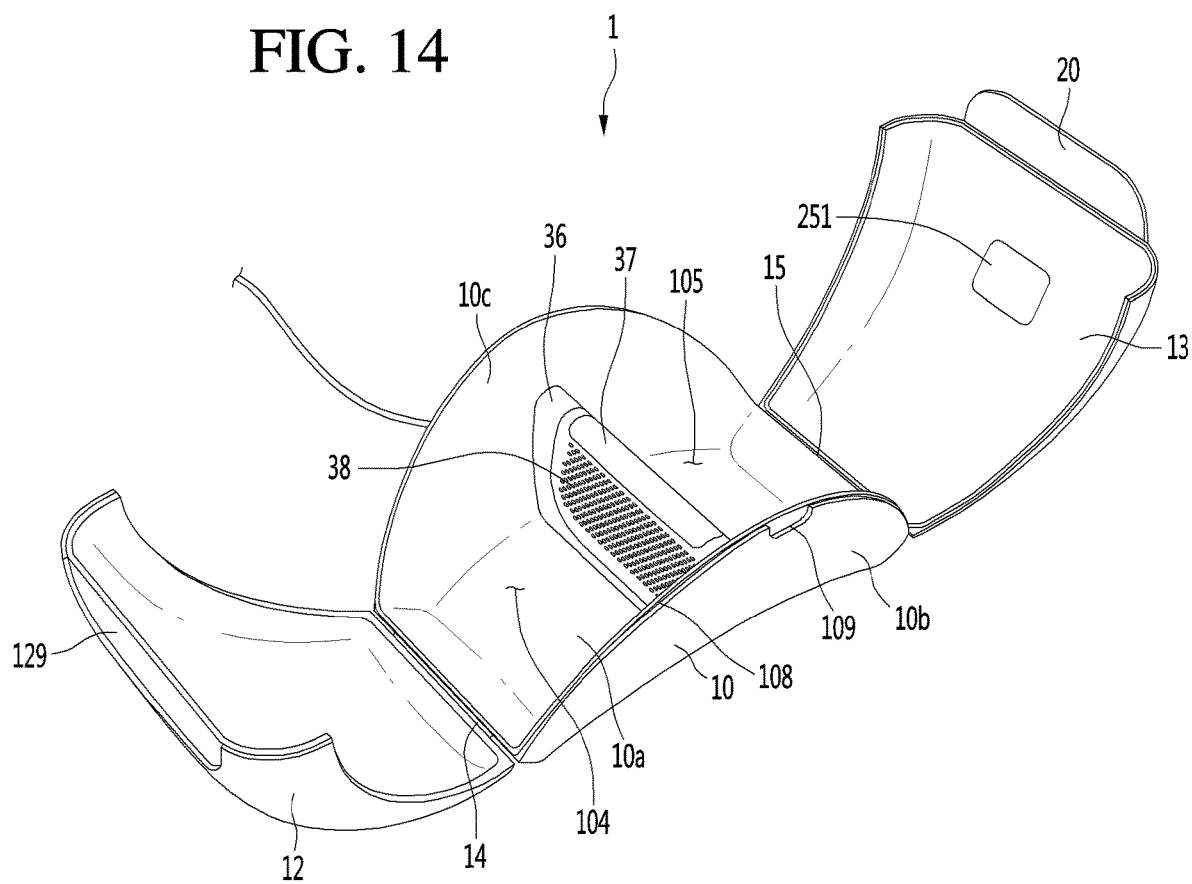
FIG. 14 is a view showing an open state of the mask storage apparatus according to a third embodiment of the present invention.
Figure 15:
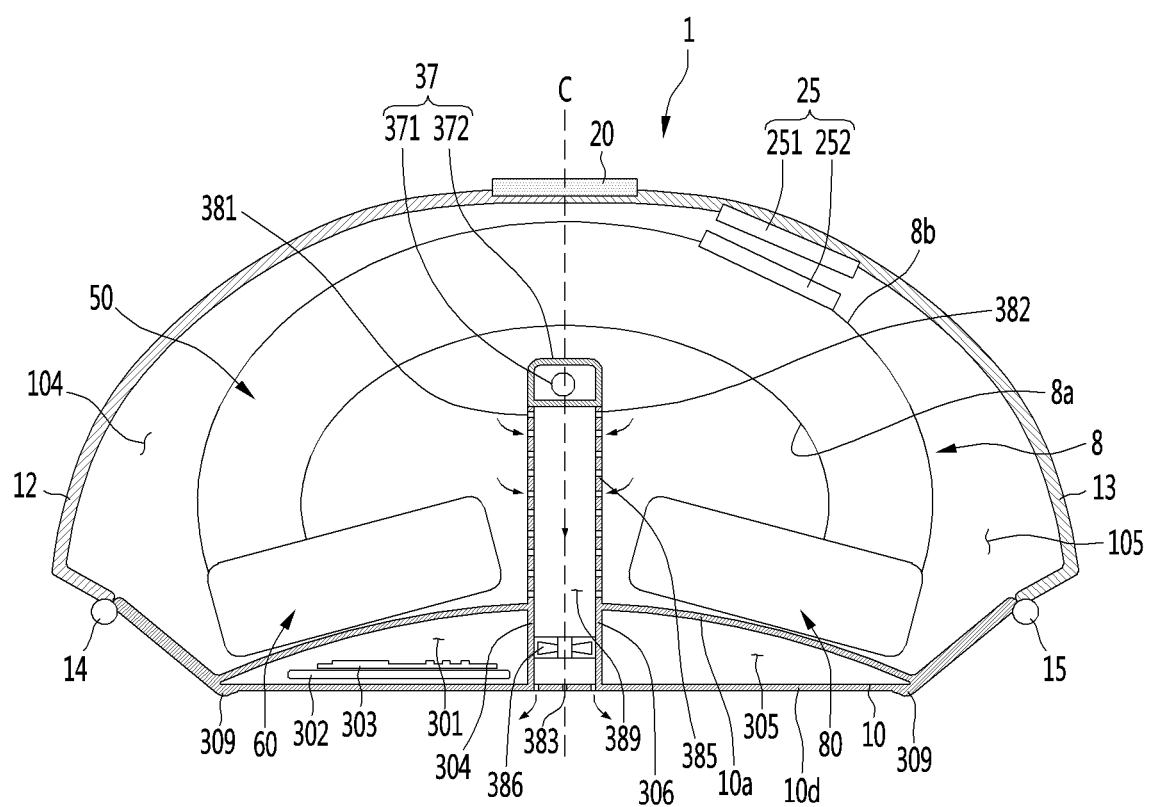
FIG. 15 is a cross-sectional view showing an internal view of the mask storage apparatus according to the third embodiment of the present invention in which a mask device is stored.

FIG. 14 is a view showing an open state of the mask storage apparatus according to a third embodiment of the present invention, and FIG. 15 is a cross-sectional view showing an internal view of the mask storage apparatus according to the third embodiment of the present invention in which the mask device is stored.

Descriptions of similar components and operations of the first embodiment that may be in the third embodiment may be omitted, and the characteristic parts of the third embodiment, such as the mask storage apparatus 1 may be described, in conjunction with the similar components and operations of the first embodiment.

Referring to FIGS. 14 and 15, the mask storage apparatus 1 according to the embodiment of the present invention includes a device storage body 10 forming a body, and a device storage cover 11 for covering the device storage body 10. The device storage cover 11 may open or close the device storage body 10.

The device storage body 10 includes a first bottom surface 10a on which the mask device 8 is supported, and side surfaces 10b and 10c extending upwardly from the first bottom surface 10a.

The first bottom surface 10a is formed with sufficient area so that the mask device 8 may be supported. A portion of the first bottom surface 10a may be spaced upwardly from the ground. For example, the first bottom surface 10a may be formed in a convex shape with a portion protruding upward. Accordingly, the first bottom surface 10a may include a round surface having a constant radius of curvature going from end portions towards the center.

The side surfaces 10b and 10c extend upward from the edge of the first bottom surface 10a. The side surfaces 10b and 10c prevent the mask device 8 supported on the first bottom surface 10a from deviating from the sides of the device storage body 10. That is, the side surfaces 10b and 10c protrude from a portion of the edge of the first bottom surface 10a to a predetermined height to support the mask device 8 from the sides.

In the present embodiment, the side surfaces 10b and 10c include a first side surface 10b and a second side surface 10c extending upward along the length direction at the edge of the first bottom surface 10a. The first side surface 10b extends upward along the longitudinal direction from one edge of the first bottom surface 10a and the second side surface 10c extends upward along the longitudinal direction from the other edge of the first bottom surface 10a. Accordingly, the first side surface 10b and the second side surface 10c are disposed to face each other.

Each end of the first side surface 10b and the second side surface 10c may be rounded. For example, an upper end portion of each of the first side surface 10b and the second side surface 10c may be rounded to have a predetermined curvature. The first side surface 10b and the second side surface 10c may have a semicircle or half-moon shape. The rounded upper end portions of the first side surface 10b and the second side surface 10c may be in contact with the device storage cover 11.

The device storage body 10 further includes a second bottom surface 10d provided below the first bottom surface 10a. The second bottom surface 10d is a portion which will be substantially in contact with the ground and supported. The second bottom surface 10d may have a flat plate shape. Both ends of the second bottom surface 10d may be connected to both ends of the first bottom surface 10a. Accordingly, internal spaces 301 and 305 may be formed between the first bottom surface 10a and the second bottom surface 10d.

The inner spaces 301 and 305 may include a first inner space 301 and a second inner space 305. For example, a portion of the first bottom surface 10a may be opened, and connection portions 304 and 306 may be provided to connect between the first bottom surface 10a and the second bottom surface 10d. Accordingly, the first internal space 301 and the second internal space 305 may be formed in the device storage body 10.

The connection portions 304 and 306 may extend downward from the edge of the opening formed in the first bottom surface 10a. The connection portions 304 and 306 may be a first connection portion 304 extending downward from one side of the opening formed in the first bottom surface 10a and a second connection portion 306 extending downward from the other side of the opening formed in the first bottom surface 10a.

The first connection portion 304 may be provided as a rib extending vertically from one side of the opening toward the second bottom surface 10d. The second connection portion 306 may be provided as a rib extending vertically from the other side of the opening toward the second bottom surface 10d. The first bottom surface 10a, the second bottom surface 10d, and the connecting portions 304 and 306 may be integrally formed.

The battery 302 and the circuit board 303 may be disposed in the first internal space 301 and the second internal space 305. The battery 302 may supply power to the mask storage apparatus 1. The circuit board 303 may control the operation of the mask storage apparatus 1.

In the present embodiment, both the circuit board 303 and the battery 302 may be disposed in the first internal space 301. The second internal space 305 may be used as a storage space for storing articles. When the second internal space 305 is used as an article storage space, one side of the device storage body 10 may be provided with an open and closeable door.

Alternatively, the circuit board 303 may be disposed in the first internal space 301, and the battery 302 may be disposed in the second internal space 305. When the circuit board 303 and the battery 302 are disposed separately, as above, heat generated from the circuit board 303 and heat generated from the battery 302 may not interfere with each other. Since the weight of the circuit board 303 and the battery 302 may be evenly distributed at both sides, the load of the mask storage apparatus 1 may be evenly distributed.

The mask storage apparatus 1 comprises a compartment. The compartment may be formed inside the device storage body 10. The compartment may protrude in a central direction from the inner surface of the device storage body 10. The compartment may divide the accommodation space of the device storage body 10 into a first accommodation space 104 and a second accommodation space 105.

The first accommodation space 104 may be a space in which a part of the mask device 8 is accommodated. The second accommodation space 105 may be a space in which the remaining part of the mask device 8 is accommodated. The first accommodation space 104 may be defined as a space formed in one side of the compartment and the first cover 12. The second accommodation space 105 may be defined as a space formed between the other side of the compartment and the second cover 13.

The compartment comprises a protrusion 36. The protrusion 36 protrudes from the first bottom surface 10a and/or the side surfaces 10b and 10c of the device storage body 10. The protrusion 36 extends upwardly from a portion of the first bottom surface 10a and may be connected to the first side surface 10b and the second side surface 10c.

Alternatively, the protrusion 36 may protrude in the direction from the inner surface of the device storage body 10 toward the open surface of the device storage body 10. The protrusion 36 may extend in a direction from one side of the inner surface of the device storage body 10 toward the other side of the inner surface of the device storage body 10. The protrusion 36 may be formed in a stepped shape formed on an inner surface of the device storage body 10.

The compartment may include a sterilization module 37. The sterilization module 37 may include a sterilizing lamp 371 for generating sterilizing light and a lamp cover 372 for covering the sterilizing lamp 371. The lamp cover 372 may be disposed above an air cover 385 to be described later, and the sterilizing lamp 371 may be disposed inside the lamp cover 372.

The sterilization module 37 may operate when the device storage cover 11 is closed after the mask device 8 is seated inside the device storage body 10. When the device storage cover 11 is opened, the operation of the sterilization module 37 may be stopped. According to this structure, it is possible to prevent an accident that may occur by operating the sterilization module 37 when the device storage cover 11 is open.

The compartment may include an air module 38. The air module 38 may forcibly circulate the internal air of the device storage body 10. The air module 38 may suck the internal air of the accommodation space and discharge the sucked internal air back into the accommodation space. Alternatively, the air module 38 may suck the air inside the accommodation space and discharge the sucked air outside of the device storage body 10.

The compartment may be the protrusion 36 itself. Alternatively, the compartment may be a configuration including the protrusion 36 and the air module 38. That is, the protrusion 36 may function as the compartment, and the air module 38 may function as the compartment.

The air module 38 may include the air cover 385 in which a plurality of air inlets 381 and 382 are formed. The air cover 385 extends in the vertical direction and may extend in the width direction of the device storage body 10. An air passage 389 is formed in the air cover 385 that connects to the air inlets 381 and 382.

The air cover 385 may be seated on a seating surface formed by the protrusion 36. Alternatively, the air cover 385 may be inserted into an opening formed at the first bottom surface 10a. The air cover 385 may be detachably mounted to the first bottom surface 10a.

The air inlets 381 and 382 may include a first air inlet 381 and a second air inlet 382. The first air inlet 381 and the second air inlet 382 may be formed on different surfaces of the air cover 385. For example, the first air inlet 381 may be formed on a first surface of the air cover 385, and the second air inlet 382 may be formed on a second surface of the air cover 385.

The first surface and the second surface of the air cover 385 may face opposite to each other. That is, the first air inlet 381 may be disposed to face the first accommodation space 104, and the second air inlet 382 may be disposed to face the second accommodation space 105. Accordingly, air in the first accommodation space 104 may be sucked into the air passage 389 of the air cover 385 through the first air inlet 381, and air in the second accommodation space 105 may be sucked into the air passage 389 of the air cover 385 through the second air inlet 382.

The mask storage apparatus 1 may include a air outlet 383 through which air inside the mask storage apparatus 1 may be discharged to the outside environment. The air outlet 383 may be a passage for discharging the air sucked into the air passage 389 of the air cover 385 to the outside of the mask storage apparatus 1. In the present embodiment, a plurality of air outlets 383 may be formed on the second bottom surface 10d of the device storage body 10. The air outlets 383 may be connected to the air passage 389 of the air cover 385. The air sucked into the air passage 389 from the first accommodation space 104 and the second accommodation space 105 may be discharged to the outside of the mask storage apparatus 1 through the air outlets 383.

A lower portion of the device storage body 10 may be provided with a support portion 309 allowing the air discharged through the air outlets 383 to smoothly flow out. The support portion 309 may protrude downward from the second bottom surface 10d such that the lower portion of the storage device body 10 and the ground are spaced apart from each other.

The air module 38 further includes a fan module 386. The fan module 386 may be disposed in the air passage 389 of the air cover 385. The fan module 386 may be disposed at a lower portion of the air passage 389. The fan module 386 may be disposed in the air passage 389 to be close to the air outlets 383. Alternatively, the fan module 386 may be disposed at a portion between to the air inlets 381 and 382 and the air outlets 383. The fan module 386 may include a fan and a motor to rotate the fan. When the fan module 386 is operated, air in the first accommodating space 104 and the second accommodating space 105 may be sucked through the first air inlet 381 and the second air inlet 382 and into the air passage 389. The air in the air passage 389 may be discharged to the outside of the mask storage apparatus 1 through the fan module 386 and through the air outlets 383. That is, the air module 38 according to the embodiment may suck the air containing the foreign matter sterilized by the sterilization module 37 and discharge the contaminated air to the outside of the mask storage apparatus 1. Since the contaminated air is discharged to the outside of the mask storage apparatus 1, the mask device 8 may be sterilized and dried.

Figure 16:
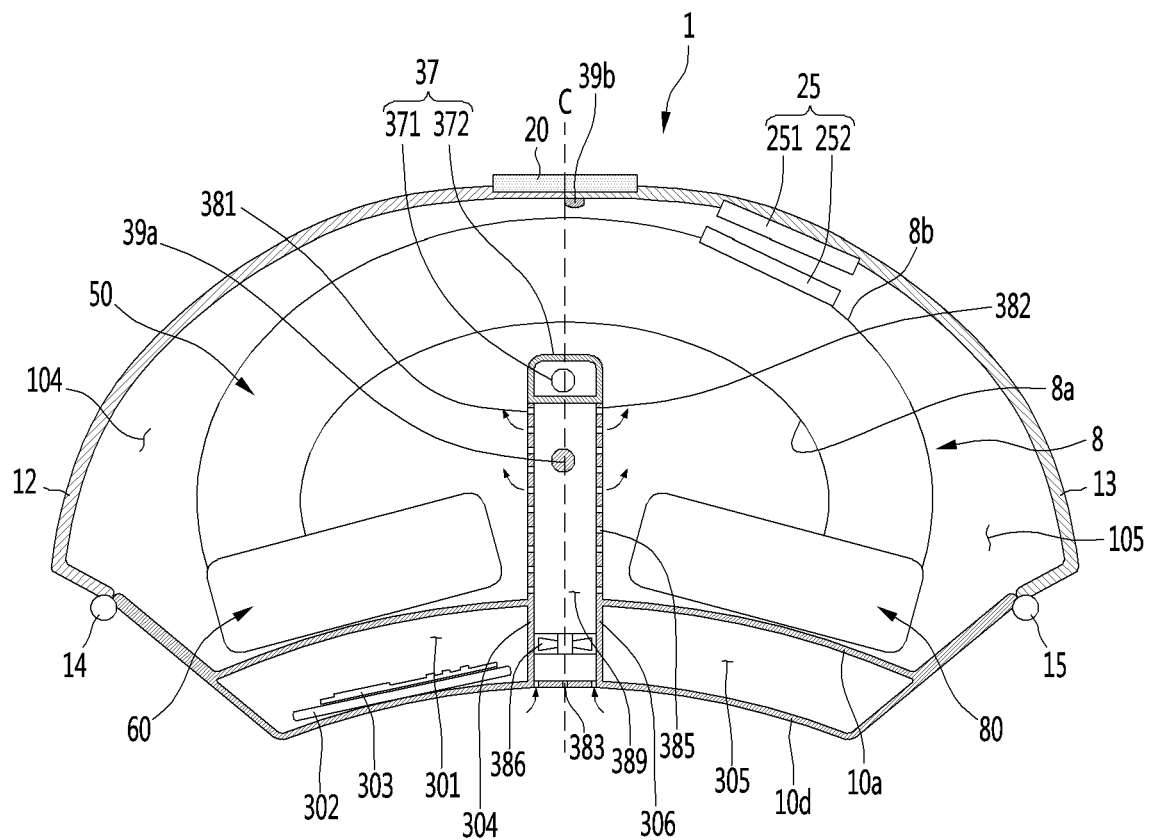
FIG. 16 is a cross-sectional view showing an internal view of the mask storage apparatus according to a fourth embodiment of the present invention in which a mask device is stored.

FIG. 16 is a cross-sectional view showing an internal view of a mask storage apparatus 1 according to a fourth embodiment of the present invention in which a mask device 8 is stored.

Descriptions of similar components and operations of the third embodiment that may be in the fourth embodiment may be omitted, and the characteristic parts of the fourth embodiment, such as the mask storage apparatus 1 may be described, in conjunction with the similar components and operations of the third embodiment.

Referring to FIG. 16, the mask device 8 according to the embodiment may be stored inside the mask storage apparatus 1. The mask storage apparatus 1 may include a device storage body 10 forming a body, and a device storage cover 11 for covering the device storage body 10. The device storage cover 11 may open or close the device storage body 10.

The device storage body 10 includes a first bottom surface 10a on which the mask device 8 is supported, and side surfaces 10b and 10c extending upwardly from the first bottom surface 10a. The storage device body 10 further includes a second bottom surface 10d spaced downward from the first bottom surface 10a. The second bottom surface 10d is a portion which may be substantially be in contact with the ground to support the device storage body 10. The second bottom surface 10d may have a convex shape in which the central portion protrudes upward from the edge to the central portion. That is, the center of the second bottom surface 10d and the ground may be spaced apart by a predetermined height. The second bottom surface 10d may include a round surface having a constant radius of curvature going from the ends toward the center.

Both ends of the second bottom surface 10d may be connected to both ends of the first bottom surface 10a. Accordingly, internal spaces 301 and 305 may be formed between the first bottom surface 10a and the second bottom surface 10d.

The mask storage apparatus 1 includes a sterilization module 37 and an air module 38. Since the sterilization module 37 and the air module 38 are the same as in the above-described third embodiment, description thereof will be omitted.

The mask storage apparatus 1 may include an ion generator 39a and 39b. The ion generator 39a and 39b may generate ions and eject them into the air in the device storage body 10. The ion generator 39a and 39b may be referred to as an ionizer. In the present embodiment, the ion generator 39a and 39b may include one or all of the first ion generator 39a and the second ion generator 39b. The first ion generator 39a may generate ions to one side of the mask device 8, and the second ion generator 39b may generate ions to the other outer side of the mask device 8.

The first ion generator 39a may be provided at the air module 38, and the second ion generator 39b may be provided at the device storage cover 11. The first ion generator 39a may release ions to the first surface 8a of the mask device 8, and the second ion generator 39b may release ions to the second surface 8b of the mask device 8. That is, the first ion generator 39a may be disposed under the mask device 8, and the second ion generator 39b may be disposed over the mask device 80. The first surface 8a of the mask device 8 may be the inner surface or the back surface of the mask device 8 covering the user's nose and mouth. The second surface 8b of the mask device 8 may be the outer or front surface that may be exposed to the outside environment.

Power for operating the ion generator 39a and 39b may be supplied from the battery 302. The ions generated by the ion generator 39a and 39b may remove harmful substances present on the front and rear surfaces of the mask device 8. For example, the first ion generator 39a may be disposed under the air cover 385. The first ion generator 39a may be disposed in the air passage 389.

The ions generated by the first ion generator 39a may be supplied to the first surface 8a or the rear surface of the mask device 8 through the air inlets 381 and 382 of the air cover 385. In this case, to supply the ions generated by the first ion generator 39a to the first surface 8a of the mask device 8, the fan module 386 may be not operated or the fan module 386 may reversely rotate to allow external air to flow into the interior space of the device storage body 10.

The second ion generator 39b may be provided at the inner surface of the device storage cover 11. The second ion generator 39b may be disposed on either the first cover 12 or the second cover 13. The second ion generator 39b may face the second surface 8b or the entire surface of the mask device 8 when the mask device 8 is stored in the mask storage apparatus 1.

When the device storage cover 11 is closed, the second ion generator 39b may supply ions to the second surface 8b of the mask device 8. By this structure, harmful substances present in the front and rear surfaces of the mask device 8 may be effectively removed by ions.

The mask device 8 may operate when stored inside the mask storage apparatus 1. That is, the first air cleaner 60 and the second air cleaner 80 of the mask device 8 may operate when stored in the mask storage apparatus 1. When the first air cleaner 60 and the second air cleaner 80 are operated, the pressure of the internal space of the mask storage apparatus 1 may increase. When the pressure of the internal space of the mask storage device 1 is increased, air in the internal space may flow into the air inlets 381 and 382, through the air passage 389, and discharged to the outside of the mask storage apparatus 1 through the air outlets 383. In this case, even when the fan module 386 of the mask storage apparatus 1 is not operated, the internal air of the mask storage apparatus 1 may be discharged to the outside environment.

Figure 17:
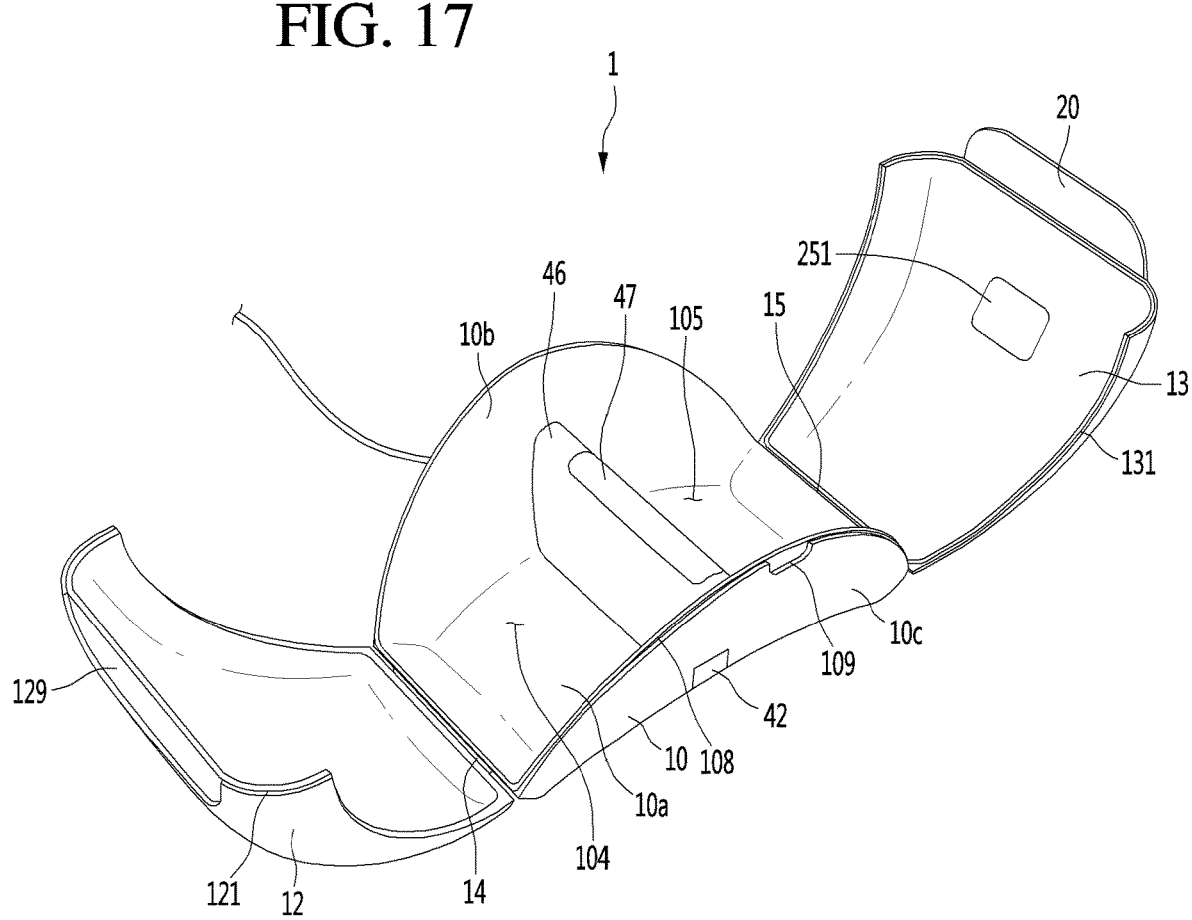
FIG. 17 is a view showing an opening state of a mask storage apparatus according to a fifth embodiment of the present invention.
Figure 18:
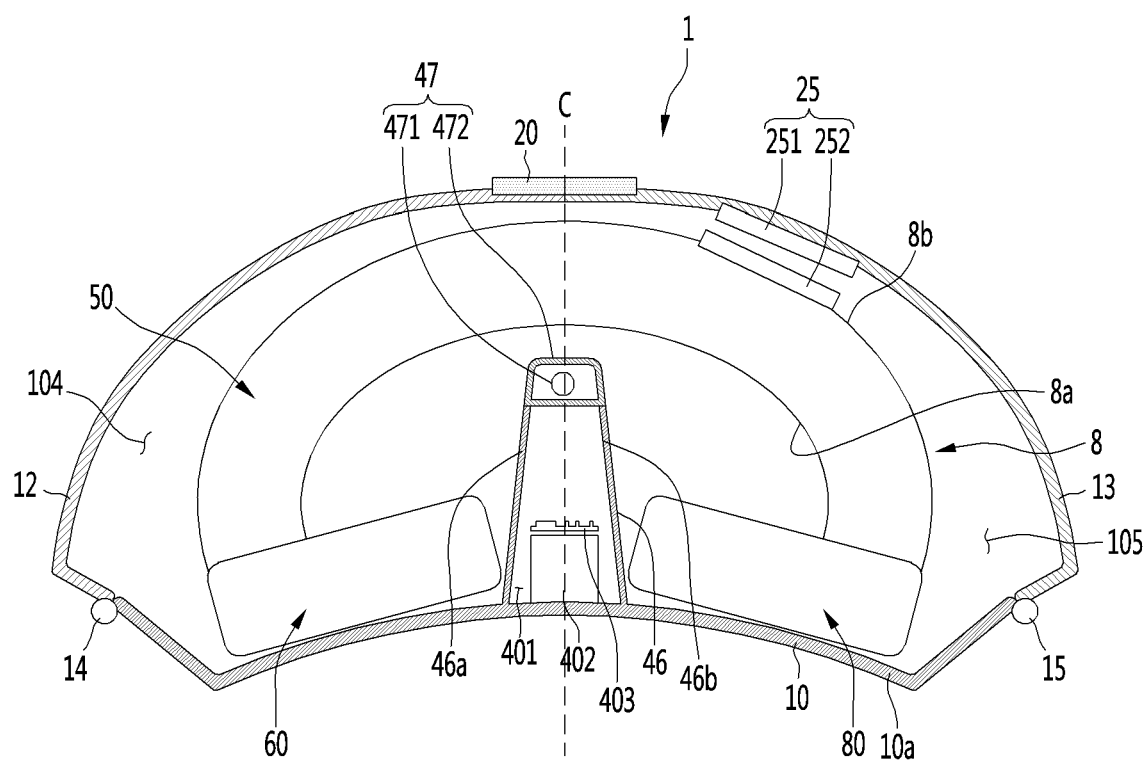
FIG. 18 is a cross-sectional view showing an internal view of the mask storage device according to the fifth embodiment of the present invention in which a mask device is stored.

FIG. 17 is a view showing an open state of the mask storage apparatus 1 according to a fifth embodiment of the present invention, and FIG. 18 is a cross-sectional view showing an internal view of the mask storage according to the fifth embodiment of the present invention device in which the mask device 8 is stored.

Descriptions of similar components and operations of the first embodiment that may be in the fifth embodiment may be omitted, and the characteristic parts of the fifth embodiment, such as the mask storage apparatus 1 may be described, in conjunction with the similar components and operations of the first embodiment.

Referring to FIGS. 17 and 18, the mask device 8 according to the embodiment is stored inside the mask storage apparatus 1. The mask storage apparatus 1 may include a device storage body 10 forming a body, and a device storage cover 11 for covering the device storage body 10. The device storage cover 11 may open or close the device storage body 10.

The mask storage apparatus 1 includes a compartment rib 46. The compartment rib 46 may be disposed in the device storage body 10. The compartment rib 46 is formed to extend upward from the bottom surface 10*a* of the device storage body 10. The compartment rib 46 extends in the width direction of the device storage device body 10 so that both ends of the compartment rib 46 may be connected to both side surfaces 10*b* and 10*c* of the device storage body 10. The compartment rib 46 may partition the inside of the device storage body 10 into a first accommodation space 104 and a second accommodation space 105.

In the present embodiment, the compartment rib 46 may be disposed at the center of the device storage body 10. The compartment rib 46 may be formed at an intermediate point that bisects the first bottom surface 10*a*. The compartment rib 46 may be formed to be inclined from the bottom to the top along two sides of the compartment rib 46. The compartment rib 46 is formed such that the horizontal cross-sectional area decreases going from bottom to top.

The compartment rib 46 may include a first rib part 46*a* and a second rib part 46*b*. The first rib part 46*a* of the compartment rib 46 faces the first accommodation space 104, and the second rib part 46*b* of the compartment rib 46 faces the second accommodation space 105. The first rib part 46*a* and the second rib part 46*b* may be disposed to face opposite sides.

Referring FIG. 18, the first rib part 46*a* may be disposed on the left side, and the second rib part 46*b* may be disposed on the right side, symmetric around a vertical center line C of the device storage body 10. In this case, the first rib part 46*a* may be formed to be inclined closer to the vertical center line C going from the lower part to the upper part. The second rib part 46*b* may be formed to be inclined closer to the vertical center line C going from the bottom to the top. Accordingly, the compartment rib 46 is formed such that the distance between the lower ends of the rib parts 46*a* and 46*b* is longer than the distance between the upper ends of the ribs parts 46*a* and 46*b*.

In other words, the compartment rib 46 may have a trapezoidal shape that becomes narrower going from the bottom to the top. According to this structure, a part of the mask device 8 stored in the mask storage apparatus 1 may be supported in close contact with the lower portion of the compartment rib 46. When the device storage cover 11 is closed with the mask device 8 inside, the device storage cover 11 may press against the outer surface of the mask device 8 so that the mask device 8 may be more firmly fixed inside the device storage body 10. In other words, the mask device 8 is held by the compartment rib 46 so as not to be moved or flipped over.

The mask storage apparatus 1 may include a sterilization module 47. The sterilization module 47 may sterilize the mask device 8. The sterilization module 47 may include a sterilizing lamp 471 for generating sterilizing light and a lamp cover 472 covering the sterilizing lamp 471. The lamp cover 472 may be disposed above the compartment rib 46, and the sterilizing lamp 471 may be located inside the lamp cover 472.

The compartment rib 46 may provide an installation space 401 in which a plurality of electronic components may be accommodated. The compartment rib 46 may have a hollow shape to form the installation space 401.

The battery 402 and the circuit board 403 may be accommodated in the installation space 401. The battery 402 and the circuit board 403 may be installed on the bottom surface 10*a* of the storage body 10, and the compartment rib 46 may be seated on the bottom surface 10*a* over the battery 402 and the circuit board 403.

The circuit board 403 may control the operation of the mask storage apparatus 1. The battery 402 may supply power for operating the sterilization module 47. The battery 402 may supply power for operating the display 20 provided in the storage cover 11.

The battery 402 may supply power to the power transmitter 251 of the wireless charger 25 provided in the device storage cover 11. In this embodiment, the installation space 401 may be formed at the center of gravity of the device storage body 10. The battery 402 may be located at the center of gravity of the device storage body 10 in order to prevent the device storage body 10 from toppling.

The installation space 401 may be used as a storage space for storing articles. A storage part 42 may be formed at one side of the device storage body 10. The storage part 42 may be connected to the installation space 401. The storage part 42 may be configured to be opened or closed on one side of the storage device body 10. For example, an opening corresponding to the storage part 42 may be formed in the storage device body 10. The opening may be connected to the installation space 401. The storage part 42 may be rotatably disposed in the opening. Opening the storage part 42 may expose the installation space 401 to the outside environment. When the storage part 42 is closed, the installation space 401 may be closed to the outside environment by the storage part 42.

The mask storage apparatus 1 according to the various embodiments may sterilize the mask device 8 using the sterilization module 47. In the installation space 401 of the mask storage device 1, an article or a component for maintenance of the mask device 8 may be stored.

While preferred embodiments of the present invention have been described above with reference to the drawings, the present invention is not limited to the above-described embodiments, and it is apparent to those skilled in the art that the embodiments of the present invention may be modified without departing from the spirit and scope of the present invention. It will be understood that modifications and variations are possible. Therefore, the scope of the present invention should not be defined by the described embodiments, but should be determined by the technical spirit described in the claims.

What is claimed is:

1. A mask storage apparatus comprising:
a body including an accommodation space in which a mask device is stored;
a cover rotatably connected to the body and capable of opening and closing the accommodation space; and
a compartment extending from an inner surface of the body and partitioning the accommodation space into a first accommodation space in which a part of the mask device is accommodated, and a second accommodation space in which a remaining part of the mask device is accommodated, the compartment including an ultraviolet lamp to sterilize the mask device, wherein the body includes:
the bottom surface for supporting the mask device;
a first side surface extending upward from one side edge of the bottom surface; and
a second side surface extending upward from an other edge of the bottom surface, wherein the body has an open top and open side surfaces, and wherein the compartment extends upwards from the bottom surface and connects to the first side surface and the second side surface forming a contour corresponding to the mask device.

2. The mask storage apparatus of claim 1, wherein
th ultraviolet lamp is disposed on an upper portion of the compartment.

3. The mask storage apparatus of claim 1, wherein
the compartment includes an air module for moving air in the accommodation space of the body,
the air module includes an air cover including an air inlet through which air is sucked in and an air outlet through which the sucked air is discharged, and
an air passage connecting the air inlet and the air outlet.

4. The mask storage apparatus of claim 3, wherein
the air module is detachably seated on a seating surface of the compartment.

5. The mask storage apparatus of claim 3, wherein
the ultraviolet lamp includes a lamp cover disposed above the air cover.

6. The mask storage apparatus of claim 3, wherein
the air passage includes a fan and a motor to rotate the fan disposed in an air flow path between the air inlet and the air outlet.

7. The mask storage apparatus of claim 6, wherein the air inlet opens to an outside environment of the body.

8. The mask storage apparatus of claim 6, wherein
the air inlet includes a first air inlet and a second air inlet, and the first air inlet faces the first accommodation space and the second inlet faces the second accommodation space, and
the air outlet includes a first air outlet and a second air outlet, and the first air outlet faces the first accommodation space and the second air outlet faces the second accommodation space,
wherein the air inlet is disposed below the air outlet at the air passage with respect to a bottom surface of the body.

9. The mask storage apparatus of claim 6, wherein
the air inlet includes a first air inlet and a second air inlet, and the first air inlet faces the first accommodation space and the second inlet faces the second accommodation space, and
the air inlet is disposed above the air outlet at the air passage with respect to a bottom surface of the body.

10. The mask storage apparatus of claim 9, wherein
the air outlet includes a first air outlet and a second air outlet, and the first air outlet faces the first accommodation space and the second air outlet faces the second accommodation space.

11. The mask storage apparatus of claim 9, wherein
the air outlet opens to an outside environment of the body.

12. The mask storage apparatus of claim 6, wherein
when the fan rotates in a first direction, air flows from an upper portion of the air cover to a lower portion of the air cover, and
when the fan rotates in a second direction opposite to the first direction, the air flows from the lower portion of the air cover to the upper portion of the air cover.

13. The mask storage apparatus of claim 1, wherein
the cover includes a first cover rotatably connected at one side of the body and closing at least the first accommodation space, and a second cover rotatably connected at an other side of the body and closing at least the second accommodation space.

14. The mask storage apparatus of claim 1, wherein
a portion of a bottom of the body is protruded inwards with respect to a different portion of the bottom of the body by a predetermined height.

15. The mask storage apparatus of claim 1, further comprising:
a power transmitter provided at an inner surface of the cover for providing charging power to the mask device.

16. The mask storage apparatus of claim 1, wherein
the first side surface and the second side surface are disposed to face each other and are contactable with the cover.

17. A mask storage apparatus comprising:
a body including an accommodation space in which a mask device is stored;
a cover rotatably connected to the body and capable of opening and closing the accommodation space; and
a compartment extending from an inner surface of the body and partitioning the accommodation space into a first accommodation space in which a part of the mask device is accommodated, and a second accommodation space in which a remaining part of the mask device is accommodated,
wherein the compartment includes:
an ultraviolet lamp to sterilize the mask device, and
an ion generator to generate ions in the accommodation space of the body,
wherein the ion generator includes a first ion generator and a second ion generator, wherein
the first ion generator is provided at a lower portion of the accommodation space of the body, and
the second ion generator is provided at an upper portion of the accommodation space of the body.

18. The mask storage apparatus of claim 17, wherein
the first ion generator is disposed at the compartment, and
the second ion generator is disposed at an inner surface of the cover facing the accommodation space of the body when the cover is closed.

19. The mask storage apparatus of claim 18, wherein
the compartment including an air module including an air inlet, an air outlet, and an air passage connecting the air inlet and the air outlet, the air outlet disposed above the air inlet, wherein the first ion generator is disposed in the air passage.

20. A mask storage apparatus comprising:
a body including an accommodation space in which a mask device is stored;
a cover rotatably connected to the body and capable of opening and closing the accommodation space; and
a compartment extending from an inner surface of the body and partitioning the accommodation space into a first accommodation space in which a part of the mask device is accommodated, and a second accommodation space in which a remaining part of the mask device is accommodated,
the compartment including an ultraviolet lamp to sterilize the mask device, wherein the compartment includes an air module for moving air in the accommodation space of the body, and
wherein the air module includes:
- an air cover including an air inlet through which air is sucked in and an air outlet through which the sucked air is discharged, and
- an air passage connecting the air inlet and the air outlet.

\* \* \* \* \*